United States Patent
Franke et al.

(10) Patent No.: US 8,672,865 B2
(45) Date of Patent: *Mar. 18, 2014

(54) WEIGHT-BEARING LOWER EXTREMITY BRACE

(75) Inventors: Hans G. Franke, Incline Village, NV (US); David Salinger, Olympic Valley, CA (US); Jeff Dodd, Truckee, CA (US)

(73) Assignee: Toad Medical Corporation, Reno, NV (US)

( * ) Notice: Subject to any disclaimer, the term of this patent is extended or adjusted under 35 U.S.C. 154(b) by 96 days.

This patent is subject to a terminal disclaimer.

(21) Appl. No.: 13/247,738

(22) Filed: Sep. 28, 2011

(65) Prior Publication Data

US 2012/0083722 A1    Apr. 5, 2012

Related U.S. Application Data

(63) Continuation-in-part of application No. 12/684,573, filed on Jan. 8, 2010, now Pat. No. 8,540,655, which is a continuation of application No. PCT/US2009/037171, filed on Mar. 13, 2009, which is a continuation-in-part of application No. 12/324,185, filed on Nov. 26, 2008, now Pat. No. 8,021,316, application No. 13/247,738, which is a continuation-in-part of application No. 12/502,893, filed on Jul. 14, 2009, now Pat. No. 8,403,872, which is a continuation-in-part of application No. 12/404,104, filed on Mar. 13, 2009, now abandoned, which is a continuation-in-part of application No. 12/324,185.

(51) Int. Cl.
  *A61F 5/00*    (2006.01)
  *A61B 5/103*   (2006.01)
  *A43B 5/04*    (2006.01)

(52) U.S. Cl.
  USPC ............................ 602/23; 600/595; 36/117.5

(58) Field of Classification Search
  USPC ........ 602/23, 24, 25, 26, 27, 28, 29; 600/595, 600/587, 300
  See application file for complete search history.

(56) References Cited

U.S. PATENT DOCUMENTS 1,598,504 A  *  8/1926  Pierce et al. .................... 602/27
2,827,897 A     3/1958  Pawlowski
(Continued)

FOREIGN PATENT DOCUMENTS

FR    2432306 A1    2/1980
WO    9749359 A1   12/1997
(Continued)

OTHER PUBLICATIONS

International Search Report, PCT/US2009/037171, dated Jun. 19, 2009, 3 pages.
(Continued)

*Primary Examiner* — Patricia Bianco
*Assistant Examiner* — Tarla Patel
(74) *Attorney, Agent, or Firm* — Baker & McKenzie LLP

(57) ABSTRACT

The present disclosure relates, according to some embodiments, to a device and/or system (e.g., redistributing weight away from a subject's foot), which may comprise (a) a platform, (b) at least one vertical support fixed to the platform and extending upwardly from the platform, and (c) at least one cuff (i) configured to surround and releasably grip at least a portion of a subject's leg other than the foot and (ii) mounted (e.g., adjustably) to the at least one vertical support at a vertical position along the at least one vertical support sufficient to suspend a subject's foot in a non-weight-bearing position above the platform during ambulation, wherein the platform, the at least one vertical support, and the at least one cuff together are configured to bear at least the subject's full weight.

20 Claims, 27 Drawing Sheets

(56) References Cited

U.S. PATENT DOCUMENTS

| | | | |
|---|---|---|---|
| 3,032,033 A * | 5/1962 | Ramirez | 602/12 |
| 6,423,021 B1 | 7/2002 | Gallegos | |
| 6,792,700 B2 | 9/2004 | Gallegos | |
| 6,976,972 B2 | 12/2005 | Bradshaw | |
| 6,997,891 B1 | 2/2006 | Vecsey | |
| 7,288,076 B2 | 10/2007 | Grim et al. | |
| 7,303,537 B1 | 12/2007 | Snyder et al. | |
| 7,462,160 B2 * | 12/2008 | Nobbe et al. | 602/27 |
| 7,666,155 B1 * | 2/2010 | Jensen et al. | 602/23 |
| 7,740,602 B2 | 6/2010 | Christensen | |
| 8,021,316 B2 * | 9/2011 | Franke et al. | 602/23 |
| 8,083,704 B2 | 12/2011 | Jensen et al. | |
| 8,403,872 B2 * | 3/2013 | Franke et al. | 602/23 |
| 2003/0216675 A1 | 11/2003 | Rooney | |
| 2005/0054962 A1 | 3/2005 | Bradshaw | |
| 2005/0171461 A1 | 8/2005 | Pick | |
| 2007/0191749 A1 | 8/2007 | Barberio | |
| 2007/0293798 A1 | 12/2007 | Hu et al. | |
| 2008/0039756 A1 | 2/2008 | Thorsteinsson et al. | |
| 2008/0269656 A1 | 10/2008 | Arnold et al. | |
| 2010/0106065 A1 | 4/2010 | Ward | |
| 2010/0130898 A1 | 5/2010 | Franke et al. | |

FOREIGN PATENT DOCUMENTS

| | | |
|---|---|---|
| WO | 2005074834 A2 | 8/2005 |
| WO | 2006053283 A2 | 5/2006 |

OTHER PUBLICATIONS

International Preliminary Report on Patentability and Written Opinion, PCT/US2009/037171, dated May 31, 2011, 7 pages.

Communication pursuant to Article 94(3) EPC, EP Application No. 09789515.5, dated Nov. 22, 2013, 4 pages.

* cited by examiner

WEIGHT-BEARING LOWER EXTREMITY BRACE

CROSS-REFERENCE TO RELATED APPLICATIONS

This application is a continuation-in-part of U.S. application Ser. No. 12/502,893 filed Jul. 14, 2009, which itself is a continuation-in-part of U.S. application Ser. No. 12/404,104 filed Mar. 13, 2009, which itself is a continuation-in-part of U.S. application Ser. No. 12/324,185 filed Nov. 26, 2008, now issued as U.S. Pat. No. 8,021,316. This application also is a continuation-in-part of U.S. application Ser. No. 12/684,573 filed Jan. 8, 2010, which itself is a continuation of PCT application No. US09/037171 filed Mar. 13, 2009, which itself is a continuation-in-part of U.S. application Ser. No. 12/324,185 filed Nov. 26, 2008, now issued as U.S. Pat. No. 8,021,316. The contents of all of the above are hereby incorporated in their entirety by reference.

FIELD OF THE DISCLOSURE

The present disclosure relates, according to some embodiments, to methods, devices, and systems for ambulation of a subject having an impaired lower extremity.

BACKGROUND OF THE DISCLOSURE

Subjects unable to support their own weight due to a lower extremity impairment may resort to crutches or wheel chairs to move about. However, crutches and wheel chairs may be undesirable because of the limitations they impose on a subject's ability to use their hands. In addition, crutches and/or wheel chairs may incompletely restore mobility, and/or may be untenable in an older person due to decreased upper body strength and/or poor balance in the case of crutches.

SUMMARY

Accordingly, a need has arisen for improved ambulatory devices for subjects with impairments of the lower extremities. The present disclosure relates, according to some embodiments, to methods, devices, and systems for ambulation of a subject having an impaired lower extremity. For example, a device may comprise a lower extremity brace configured to bear a subject's weight and/or transfer the load to unimpaired organs and/or tissues.

According to some embodiments, a device and/or system (e.g., redistributing weight away from a subject's foot) may comprise (a) a platform, (b) at least one vertical support fixed to the platform and extending upwardly from the platform, and (c) at least one cuff (i) configured to surround and releasably grip at least a portion of a subject's leg other than the foot and (ii) mounted (e.g., fixedly, adjustably) to the at least one vertical support at a vertical position along the at least one vertical support sufficient to suspend a subject's foot in a non-weight-bearing position above the platform during ambulation, wherein the platform, the at least one vertical support, and the at least one cuff together are configured to bear at least the subject's full weight. A vertical support may comprise, in some embodiments, a strut positioned relative to the subject's leg on which the system is worn opposite the subject's sagittal plane or opposite the subject's coronal plane. For example, a strut may be positioned generally behind the subject's leg on which the system is worn. In some embodiments, a strut positioned generally behind the subject's leg on which the system is worn may have an S-curve profile. A vertical support may comprise, for example, a strut configured to extend along the outside of the leg on which the system is worn. In some embodiments, a vertical support may extend distal to the subject's foot (e.g., extend from about the tibial plateau to beyond the bottom of the subject's foot). In some embodiments, a cuff may comprise an anterior shell, an opposing posterior shell, and at least one tension adjustment fastener configured to releasably connect the anterior shell and the posterior shell, wherein the anterior shell and the posterior shell are configured to combine to surround the circumference of the subject's leg. In some embodiments, alignment or guide pins may be used to guide the anterior and posterior shells into proper alignment and to provide further support for the device when it is surrounding the circumference of the subject's leg. A cuff may comprise at least one collar (e.g., adjustably mounted to the at least one vertical support), according to some embodiments. A collar may have, in some embodiments, opposing ends spaced apart and a tension adjustment fastener corresponding to each collar, each tension adjustment fastener configured to releasably connect the opposing ends of the corresponding collar, wherein each collar and corresponding tension adjustment fastener are together configured to surround the circumference of the subject's leg.

According to some embodiments, a cuff may further comprise at least one pad shell fixed to the at least one collar, and at least one pad fixed to the at least one pad shell. A pad shell may comprise a moldable plastic selected from the group consisting of a thermoplastic, a thermosetting plastic, and combinations thereof, in some embodiments. A pad may comprise, according to some embodiments, a material selected from the group consisting of polyurethane, polyethylene, neoprene, ethylene vinyl acetate, foam, silicone, rubber, and combinations thereof. In some embodiments, a cuff may include a second pad shell fixed to the at least one collar and a second pad fixed to the second pad shell. A cuff including two pads and pad shells may be arranged such that the first pad comprises an anterior pad, the first pad shell comprises an anterior pad shell, the second pad comprises a posterior pad, and the second pad shell comprises a posterior pad shell, according to some embodiments. A cuff may be configured to extend from about the gastrocnemius/solius muscles to about the tibial plateau, according to some embodiments. A device and/or system (e.g., for redistributing weight away from a subject's foot) may comprise, in some embodiments, an outsole fixed to the platform and configured to contact the ground during ambulation. In some embodiments, an outsole may comprise a flange extending, for example, vertically along at least a portion of the back of the vertical support.

A shell (e.g., anterior shell), according to some embodiments, may comprise at least one fastener guide positioned across the anterior surface of the anterior shell and configured to receive at least a portion of the at least one tension adjustment fastener. In some embodiments, a shell (e.g., anterior shell, posterior shell) may comprise a moldable plastic selected from the group consisting of a thermoplastic, a thermosetting plastic, and combinations thereof. A shell (e.g., anterior shell, posterior shell) may be mounted (e.g., fixedly, adjustably) to the at least one vertical support in some embodiments. A shell (e.g., anterior shell, posterior shell), according to some embodiments, may include an attached pad. For example, a cuff may include one or more pads fixed to (e.g., lining) at least a portion of the surface(s) proximal to the subject's skin. Each cuff and/or each shell may include a pad. Each pad may independently comprise a material selected from the group consisting of polyurethane, polyethylene, neoprene, ethylene vinyl acetate, foam, silicone, rubber, and combinations thereof. In some embodiments, a cuff may comprise one or more bladders fixed to (e.g., lining) at least a portion of the surface(s) proximal to the subject's skin. Each cuff and/or each shell may include a bladder. Each bladder may be filled (e.g., at least partially filled, completely filled) with a fill material. A fill material may comprise a foam. A fill material may provide, for example, a cushioned and/or custom fit.

According to some embodiments, a device and/or system (e.g., for redistributing weight away from a subject's foot) may be configured to secure a subject's leg in a bent (e.g., slightly bent) position. A vertical support may comprise, for example, a vertical rod (e.g., extending distal to the subject's foot). A lateral bar may be interposed between the at least one cuff and the vertical rod, in some embodiments. A device and/or system (e.g., for redistributing weight away from a subject's foot) may comprise, according to some embodiments, a second cuff, the second cuff (a) configured to surround and releasably grip at least a second portion of a subject's leg other than the foot and (b) mounted (e.g., fixedly, adjustably) to the at least one vertical support at a vertical position along the at least one vertical support sufficient to suspend a subject's foot in a non-weight-bearing position above the platform during ambulation.

In some embodiments, a device and/or system (e.g., for redistributing weight away from a subject's foot) may comprise further (d) a hinge attached to the upper end of the vertical support, (e) a second vertical support rotatably attached to the hinge, and (f) a second cuff, the second cuff (i) configured to surround and releasably grip at least a second portion of a subject's leg other than the foot and (ii) mounted (e.g., fixedly, adjustably) to the second vertical support at a vertical position along the second vertical support sufficient to cooperate with the first cuff to suspend a subject's foot in a non-weight-bearing position above the platform during ambulation. A second cuff may be configured to extend from about the proximal patella to about the upper quadriceps. According to some embodiments, a device and/or system (e.g., for redistributing weight away from a subject's foot) may comprise a mated shoe comprising a lift configured to vertically align the suspended foot and the other foot. In some embodiments, a strut may be configured to be contiguous with its adjacent platform.

The present disclosure relates, in some embodiments, to methods for facilitating ambulation of a subject having a leg with an impaired lower extremity. A method may comprise, for example, suspending at least a portion of the impaired lower extremity in a non-weight bearing position using a load redistribution system and redistributing the weight to one or more unimpaired regions of the leg using the load redistribution system. Redistributing the weight to one or more unimpaired regions of the leg may comprise, in some embodiments, redistributing the weight to one or more lateral surfaces (e.g., unimpaired lateral surfaces) of the leg. According to some embodiments, a method may comprise adjusting the pressure applied to at least one lateral surface (e.g., by substituting with a different contact surface area). A method (e.g., for facilitating ambulation of a subject having a leg with an impaired lower extremity) may comprise, for example, contacting the leg with a load redistribution system to suspend at least the impaired lower extremity in a non-weight bearing position and redistributing at least the weight of the subject during ambulation to one or more unimpaired regions of the leg. A load redistribution system may include, in some embodiments, a platform, at least one vertical support fixed to the platform and extending upwardly from the platform, and at least one cuff mounted (e.g., fixedly, adjustably) to the at least one strut at a position sufficient to suspend the at least a portion of the impaired lower extremity in a non-weight-bearing position above the platform during ambulation, wherein the platform, the at least one strut, and the at least one cuff are configured to (a) bear at least the subject's full weight and (b) distribute the weight born to at least a portion of the subject's leg other than the subject's foot.

In some embodiments, a device and/or system (e.g., for redistributing weight away from a subject's foot) may comprise a means for suspending a subject's foot in a non-weight-bearing position and a means for redistributing a subject's weight to at least one surface on the subject's leg.

According to some embodiments, a lower extremity brace may comprise any suitable material, which may vary according each intended use and/or each component of a brace. A lower extermity brace may comprise, for example, a material selected from steel, a steel alloy, aluminum, an aluminum alloy, titanium, a titanium alloy, carbon fiber, wood, an aramid fiber, a para-aramid fiber (e.g., KEVLAR), fiberglass, plastic (e.g., rigid, semi-regid, resilient, flexible, and/or moldable), flexible, elastomeric, and/or resilient materials (e.g., polyurethane, polyethylene, neoprene, ethylene vinyl acetate, foam, silicone, rubber, and the like), and combinations thereof.

A lower extremity brace may be configured to reduce or eliminate a tuorniquet effect in some embodiments. For example, a lower extremity brace may comprise a prosthetic suspension sleve (e.g., comprising urethane and/or silicone) to provide circumferential compression, to provide skin protection, to increase suspension, and/or to minimize compression of the lower extremity.

BRIEF DESCRIPTION OF THE DRAWINGS

Some embodiments of the disclosure may be understood by referring, in part, to the present disclosure and the accompanying drawings, wherein.

DETAILED DESCRIPTION

Figure 1A:
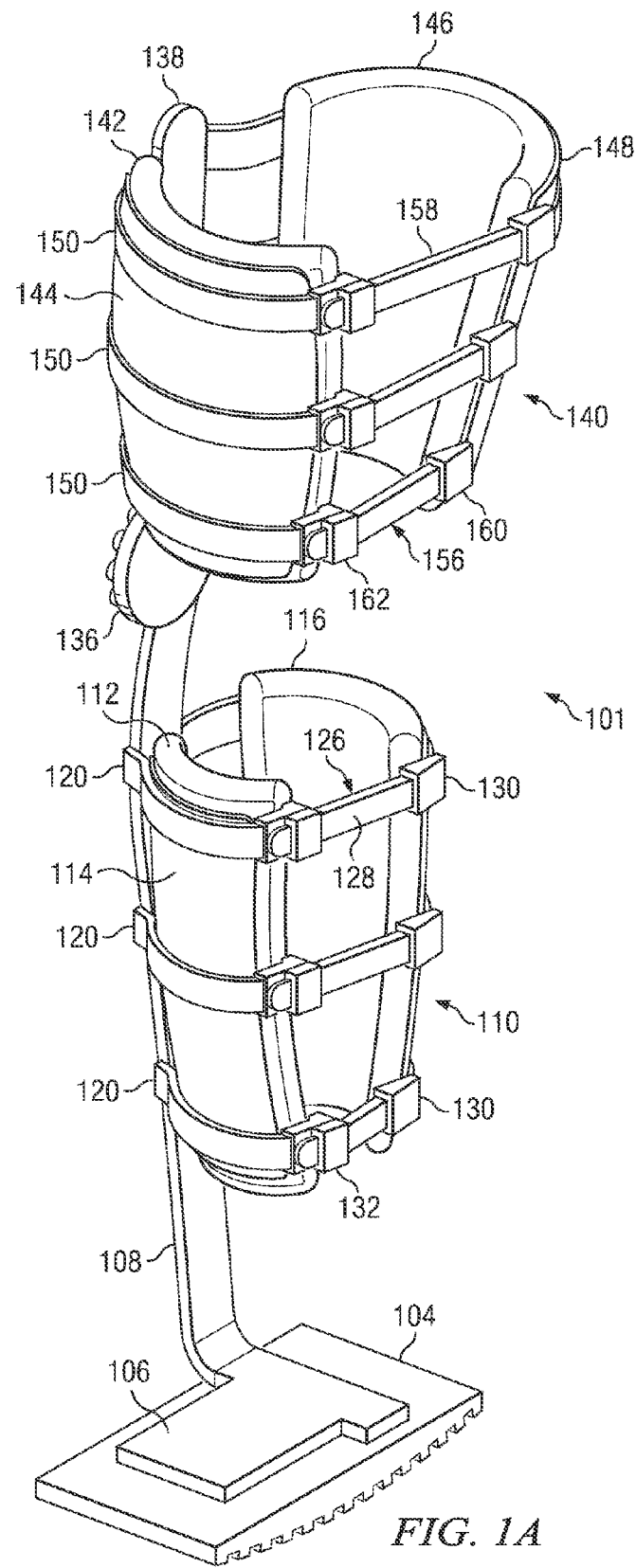
FIG. 1A illustrates a generally isometric view of a device for ambulation of a subject having an impaired lower extremity according to a specific example embodiment of the disclosure.
Figure 1B:
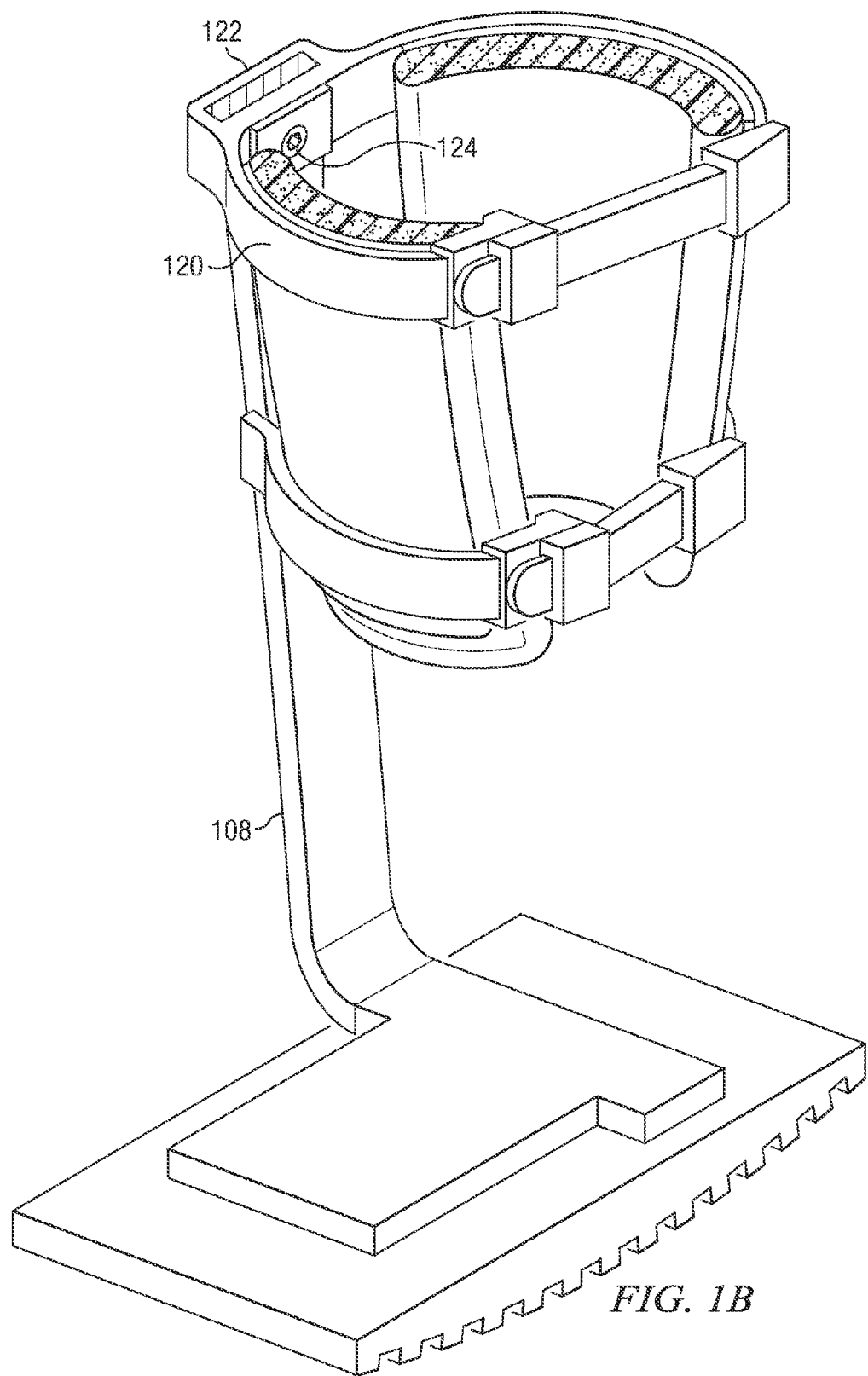
FIG. 1B illustrates a left profile view of the device for ambulation of a subject shown in FIG. 1A according to a specific example embodiment of the disclosure.
Figure 1C:
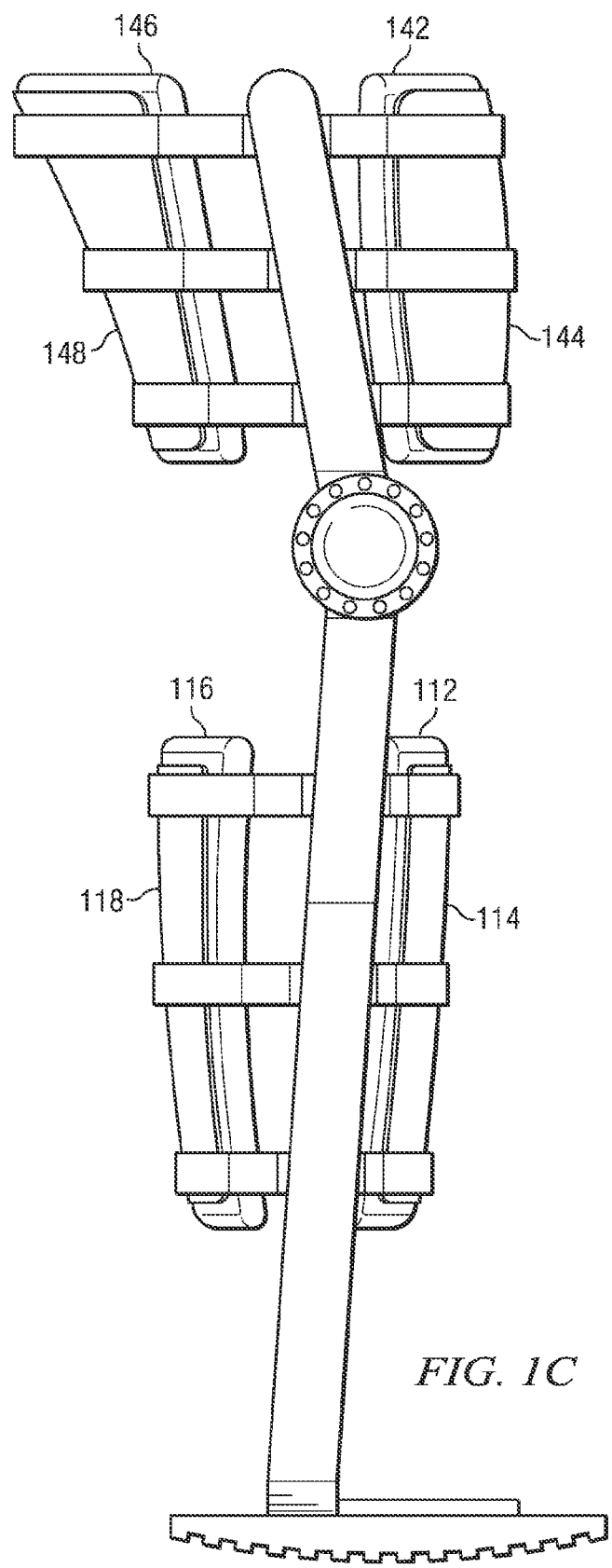
FIG. 1C illustrates a right profile view of the device for ambulation of a subject shown in FIG. 1A according to a specific example embodiment of the disclosure.
Figure 1D:
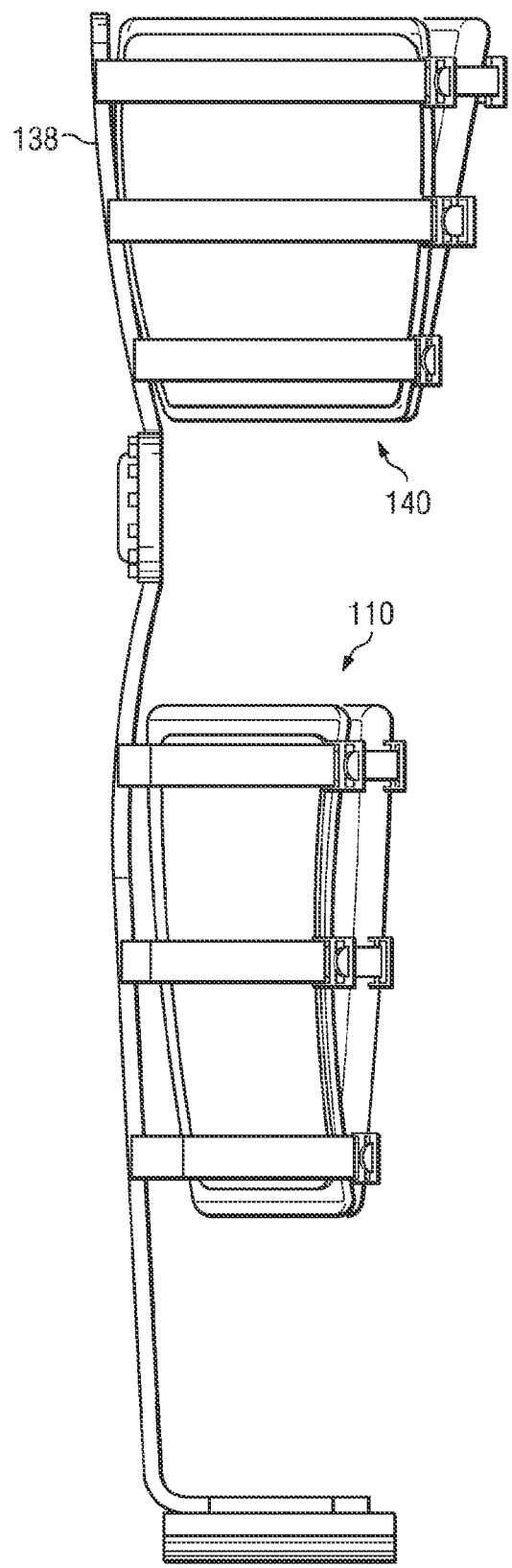
FIG. 1D illustrates a front view of the device for ambulation of a subject shown in FIG. 1A according to a specific example embodiment of the disclosure.

The present disclosure relates, according to some embodiments, to methods, devices, and systems for facilitating ambulation (e.g., walking, running, dancing, and the like) of a subject, optionally, a subject having an impaired lower extremity. For example, a system for facilitating ambulation of a subject may include a walking brace configured to suspend a subject's lower extremity (e.g., foot) in a non-weight-bearing position. In some embodiments, a system may transfer the subject's weight to at least a portion of the subject's lower leg and/or to at least a portion of the subject's upper leg. A weight-bearing portion of the lower leg may have a vertical span from about the gastrocnemius/solius muscles to about the tibial plateau. A weight-bearing portion of the upper leg may have a vertical span from just superior to the patella to about the proximal one third of the quadriceps femoris. A lower cuff may span up to the entire circumference of a subject's lower leg. An upper cuff may span up to the entire circumference of a subject's upper leg. When positioned upright, a subject's foot may dangle loosely. The subject's impaired lower extremity may have a wound dressing, a cast, a wrap, or other dressings or garments. With respect to a cast (and/or any other rigid and/or semi rigid material), care may be taken to ensure that the cast does not bear any weight since that load may be transmitted to a subject's foot. For example, a device may be adapted to accommodate a subject wearing a cast that covers the subject's ankle and extends up to about the mid-calf region (e.g., by shortening the lower cuff by an amount sufficient to ensure that weight is not transferred from the brace to the cast). It may be desirable, in some embodiments, to include a covering and/or sling to protect and support a lower extremity. The choice of covering and/or sling may be influenced by the nature of the impairment and/or the nature of the dressing.

For example, it may be desirable to support and/or immobilize a subject's foot in a position that is generally perpendicular to the axis of the lower leg (e.g., to prevent and/or minimize Achilles tendon contracture). For example, a sling attached (e.g., by a slide, spring or adjustable canvas component to avoid permitting the foot to bear weight) to at least one cuff and/or at least one strut may be used to secure a subject's foot in this position. In one example, the sling may surround the foot making contact at or in the general region of the arch. In other examples, the sling may surround the foot, making contact at the heel or the ball of the foot. The portion in contact with the foot may be of any useful material including, but not limited to, synthetic fabrics, plastics, foams (e.g., P-Cell foam), and natural products like cotton or wool. For example, polyurethane, polyethylene, neoprene, ethylene vinyl acetate, silicone, rubber, and combinations thereof may be used. If the sling is attached to the cuff and/or strut using a canvas component, the canvas length may be adjusted using any means known in the art including buckles, snaps and the like to provide the foot with the desired tension. According to some embodiments, a sling may partially or completely surround a lower extremity (e.g., a foot). A sling, in some embodiments, may be configured like an ordinary sock. A sling may be attached (e.g., removably attached) to a lower extremity brace (e.g., to a cuff, a strutt, platform, and/or elsewhere). According to some embodiments, a platform may be fitted with one or more pads on its upper surface with the pad positioned, for example, under the ball of the foot or over the entire platform. A foot pad, in some embodiments, may be scored or perforated into segments to allow a health care worker or a subject to customize the support as needed. For example, it may be desirable to minimize Achilles tendon contracture in a subject with an open sore (e.g., diabetic foot ulcer) by providing foot support that does not contact the open sore. Segments of the pad may be selectively removed to avoid that contact. A pad and/or a sling may comprise, according to some embodiments, one or more liners including, for example, a cushioned liner (e.g., a Spenco® liner), a silicon liner, and/or combinations thereof. A lower extremity brace for a subject having or at risk of having a diabetic foot ulcer, for example, may include a sling with a Spenco® liner and an additional, internal, silicon liner.

According to some embodiments, an impairment of a lower extremity may include a foot impairment, an ankle impairment, and/or a knee impairment. An impairment may affect a subject's ability to bear weight on or near the effected region. According to some embodiments, an impairment of a lower extremity may include any condition that makes it undesirable for a subject to bear weight on the extremity. For example, an impairment may exist where the pathology itself impedes the weight bearing capacity. An impairment may also exist where therapy, convalescence, and/or rehabilitation include relieving the region of weight-bearing forces. Examples of lower extremity impairments may include, without limitation, a fractured bone, a broken bone, a sprain, an ulcer (e.g., a diabetic ulcer), an amputation, a suture (e.g., on a distal end of an extremity such as the bottom of a foot or the terminus of a residual limb after an amputation), arthritis, a joint dislocation, a joint subluxation, a torn ligament (e.g., a torn anterior cruciate ligament), a torn cartilage (e.g., a torn meniscus), bursitis, tendonitis, an infection, gout, gangrene, plantar fasciitis, metabolic diseases, bone or cartilage diseases, neuropathic states and/or post-operative states. With regard to amputation, a lower extremity brace may be used, according to some embodiments, as an intermediate step device prior to a permanent below the knee prosthesis, such as waiting for the maturing of the residual limb. In some embodiments, a lower extremity brace may be used as a permanent, below-the-knee prosthesis, for example, those with a very low amputation. A lower extremity brace may be used as a temporary prosthesis for those with residual limb wounds, or those with residual limb breakdown in some embodiments. A lower extremity brace may be used as a post operative protector with a thigh component spanning above the knee to reduce contracture while the brace increases compression to reduce swelling and improve healing. A thigh segment may be removed or articulated below the knee joint to allow for early ambulation of the amputee while the open distal end of the brace will provide relief for the suture site.

In some embodiments, increased ambulation may reduce, eliminate, and/or prevent one or more conditions, including, for example, deep venous thrombosis, atrophy, pain (e.g., lower back pain due to bed rest), and/or osteoporosis or other bone loss. Increasing a subject's ambulation without crutches may decrease the incidence of injuries associated with falling and/or upper body strain.

A load redistribution system, in some embodiments, may include a platform, at least one vertical strut fixed to the platform, and at least one cuff fixed to the at least one vertical strut. In some embodiments, one or more fasteners may be used to secure a load redistribution system to a subject's leg including, for example, belts, buckles (e.g., ski boot buckles, ratcheting buckles), buttons, cams, carabineers, chains, cinches, clasps, D-rings, draw-strings, hooks, levers, locks, loops, slides, snaps, straps, and/or tensioners. These fasteners may be attached to the at least one vertical strut and/or the at least one cuff In some embodiments, alignment or guide pins may be used in the at least one cuff to guide cuff components into proper alignment with each other and to provide further support for the device when it is surrounding the circumference of at least a portion of the subject's leg. For example, a system comprising two cuffs configured to contact each other along at least one edge, may include one or more guide pins (e.g., positioned generally perpendicular to the at least one edge) on one cuff and corresponding guide apertures (e.g., sleeves) on the other cuff In some embodiments, a guide pin may slide releasably in a corresponding guide aperture. A system may include any desired or required number of guide pins and corresponding guide apertures (e.g., from about 1 pair to about 20 pairs). According to some embodiments, all guide pins may be arranged on one cuff and all guide apertures may be located on a facing cuff In some embodiments, a mixture of guide pins and apertures may be arranged on one cuff with the corresponding guide apertures and guide pins arranged on the other cuff One or more guide pins and corresponding guide apertures may be included in a system having a single cuff (e.g., a hinged cuff or clam-shell cuff).

According to some embodiments, a load redistribution system may be configured to bear and/or redistribute a load (e.g., a subject's weight). For example, a load redistribution system may be configured to transfer the load of s subject's weight away from the subject's foot and transfer it to the subject's lower and/or upper leg. A load redistribution system may comprise one or more struts positioned adjacent to a subject's leg (e.g., in front of, behind, to the right, of and/or to the left of a subject's leg). For example, a single strut may be positioned on the left side of a left leg, on the right side of a right leg, or behind a left leg or right leg. In some embodiments, a strut may be positioned on the generally opposite side of a leg from a subject's sagittal plane or on the generally opposite side of a leg from a subject's coronal plane. In some embodiments, a strut positioned generally behind the subject's leg on which the system is worn may have an S-curve profile. For example, a strut may be configured to have a profile that resembles a letter "S" in that it has two opposing inflection points (e.g., one anterior and one posterior). An S-curve profile may permit clearance for a subject's foot and/or a normal stride.

A strut may comprise, according to some embodiments, two pieces (e.g., an upper piece and a lower piece) joined by a hinge. In some embodiments, a hinge may be configured to permit a limited range (e.g., limited flexion and/or extension) and/or an unlimited range of rotational motion. According to some embodiments, a two-strut system may have a strut on each side of a subject's leg, with each strut having a single piece (e.g., lower leg only) or two pieces connected by a hinge (e.g., a full leg brace).

According to some embodiments, a load redistribution system may be configured to bear a load. A load may include, for example, a subject's weight, a portion of a subject's weight, and/or a multiple of a subject's weight (e.g., 1.1×, 1.2×, 1.5×, and/or 2×). It may be desirable for a load redistribution system to bear a more than a subject's weight, for example, where the subject may carry additional weight (e.g., a backpack, a bag of groceries, a child, and/or the like) and/or may put the system under additional stress (e.g., through sport, exercise, or the like). In some embodiments, a subject's lower extremity (e.g., foot) with a load redistribution system in place bears little or no weight, even though weight is born by that leg (e.g., while standing, exercising, working, and/or engaging in other activities).

A load redistribution system may include at least one cuff fixed to at least one strut in some embodiments. For example, a system may include a lower leg cuff and an upper leg cuff. A system may include a plurality of lower cuffs and/or a plurality of upper cuffs in some embodiments. For example, if a single cuff would contact and/or cover an injured portion of a lower leg, it may be desirable to instead use two or more lower cuffs configured to minimize and/or avoid contacting/covering the affected region. A cuff may be fixedly or adjustably mounted to a corresponding strut in some embodiments. For example, a strut may include a series of holes (e.g., equidistantly spaced) configured to receive a corresponding pin (e.g., spring-loaded) and/or screw attached to a cuff. A user may slide the cuff along the length of a strut and engage the screw and/or pin when a desired position is found. In some embodiments, a load redistribution system may include continuously variable adjustment system. A cuff may slide along the length of a strut with one or more set screws configured to fix the relative positions of each once a desirable position is found.

In some embodiments, a cuff may include a pad disposed to contact at least a portion of a subject's leg and an outer shell. An inner pad may comprise any desirable gel, foam (e.g., P-Cell foam), and/or other cushioning material(s). A custom fit cuff may facilitate, according to some embodiments, uniform distribution (e.g., uniform, substantially uniform, relatively uniform) of a subject's weight over the surface area of the cuff. An outer shell may comprise a moldable material.

In some embodiments, a cuff may be opened on at least one side to facilitate donning and/or removing the cuff (and attached load redistribution system). For example, a cuff may comprise two outer shells with one or more hinges arranged on one side to allow the cuff to open clamshell-style. Two or more outer shells may fit together without a hinge or other permanent connection according to some embodiments. Once donned, a cuff may be closed and/or secured using any type of fixed or adjustable tensioning system. For example, one or more collars, straps, cinches, guides, loops, hooks, hoops, buckles, and/or combinations thereof may be used. In some embodiments, a tensioning system may include hooks and/or loops (e.g., VELCRO®).

According to some embodiments, a load redistribution system, when donned, will increase a subject's inseam. This may result in an undesirable difference between the inseam of the leg on which a load redistribution system is worn and the inseam of the free leg. Any difference may be offset, at least partially, by wearing a lift (e.g., integrated and/or inserted in a shoe) or other apparatus on the free leg.

FIGS. 1A-1D illustrate an example of a load redistribution system 101 for ambulation of a subject having a lower extremity impairment, in accordance with embodiments of the present disclosure. As shown in FIGS. 1A-1D, load redistribution system 101 may include outsole 104, platform 106, lower strut 108, lower cuff 110, hinge 136, upper strut 138, and upper cuff 140.

Outsole 104 may comprise a foot pad, the bottom of which may be rounded (e.g., rocker outsole) to facilitate walking. The bottom may be ridged as pictured or may have another tread pattern to aid ambulation. Outsole 104 may comprise a hard rubber or other suitable material. Outsole 104 may be generally rectangular in shape as depicted. Other regular and/or irregular shapes may be suitable and/or desirable in some embodiments. Platform 106 may be contiguous with lower strut 108 as shown or may be a separate piece fixedly attached (e.g., welded, bolted) to lower strut 108. In some embodiments, outsole 104 and platform 106 may be adjustable (e.g., fore and aft) relative to each other. The lower surface of platform 106 may be affixed to outsole 104 with any type of fastener and/or adhesive. Platform 106 may sit atop outsole 104 as shown. In some embodiments, platform 106 may be recessed within outsole 104, for example, so that the upper surface of outsole 104 is flush with the upper surface of platform 106. Platform 106 may have any regular or irregular shape. Platform 106 may be somewhat smaller than outsole 104 as depicted or may be sized to match the size of outsole 104. In some embodiments, it may be desirable for platform 106 to be larger than outsole 104. Platform 106 may comprise a rigid material suitable for bearing a subject's weight. Examples of such materials include, without limitation, steel, a steel alloy, aluminum, an aluminum alloy, titanium, a titanium alloy, carbon fiber, wood, an aramid fiber, a para-aramid fiber (e.g., KEVLAR), fiberglass, and combinations thereof.

Lower strut 108 may extend vertically from platform 106 to hinge 136. Upper strut 138 may extend vertically from hinge 136 to a position corresponding to or just below a subject's hip. Lower strut 108 may have a lengthwise axis that is approximately parallel to the lengthwise axis of a subject's leg (e.g., lower leg). Upper strut 138 may have a lengthwise axis that is approximately parallel to the lengthwise axis of a subject's leg (e.g., upper leg). Lower strut 108 and/or upper strut 138 may comprise one or more rigid materials capable of bearing a subject's weight. Examples of such materials include, without limitation, steel, a steel alloy, aluminum, an aluminum alloy, titanium, a titanium alloy, carbon fiber, wood, an aramid fiber, a para-aramid fiber (e.g., KEVLAR), fiberglass, and combinations thereof.

As depicted, lower cuff 110 may comprise anterior pad 112, anterior pad shell 114, posterior pad 116, posterior pad shell 118, calf collar 120, and tension adjustment fastener 126. Pads 112 and/or 116 may independently comprise flexible, elastomeric, and/or resilient materials including, for example, polyurethane, polyethylene, neoprene, ethylene vinyl acetate, foam (e.g., P-Cell foam), silicone, rubber, and the like. Pad shells 114 and/or 118 may independently comprise a moldable plastic. In some embodiments, pad shells 114 and/or 118 may independently comprise steel, a steel alloy, aluminum, an aluminum alloy, titanium, a titanium alloy, carbon fiber, an aramid fiber, a para-aramid fiber (e.g., KEVLAR), fiberglass, and combinations thereof Pad shells 114 and/or 118 comprising a moldable material may be custom fit to a subject. A moldable plastic may include, for example, a thermoplastic (e.g., capable of more than one cycle of melting, molding, and setting) and/or a thermosetting plastic (e.g., capable of one cycle of melting, molding, and setting). Pads 112 and/or 116 may be adhered, welded, bonded, stitched, or otherwise fixed to pad shells 114 and/or 118, respectively.

Pad shells 114 and/or 118 may be fixedly attached to calf collar 120. Calf collar 120 may extend up to all the way around the circumference of a subject's lower leg. Calf collar 120 may include sleeve 122 positioned, for example, at or near its midpoint. Sleeve 122 may be configured to receive strut 108. Sleeve 122 may have a cavity, the longitudinal axis of which is about perpendicular to the lengthwise axis of strut 108. Sleeve 122 may be configured to allow collar 120 to slide along the length of strut 108. Sleeve 122 may include set screw 124 positioned to adjustably contact strut 108. Each calf collar may be configured to include a sleeve and each sleeve may include a set screw. In use, set screw 124 may be loosened to permit collar 120 to slide along the length of strut 108. Once a desirable position is found, set screw 124 may be tightened to fix the position of collar 120 on strut 108. Set screw 124 may be positioned on the inside of collar 120 and directed outwardly toward strut 108 as shown. In some embodiments, set screw 124 may be positioned on the outside of collar 120 and directed inwardly toward strut 108. As depicted, lower cuff 110 may include three calf collars 120. In some embodiments, more or fewer collars may be desired and/or required.

Tension adjustment fastener 126 may include strap 128, cinch 130, and anchor 132. Strap 128 may be fixed to one end of calf collar 120 via anchor 132. Cinch 130 may be fixed to the other end of collar 120. Cinch 130 may be configured to receive and releasably grip strap 128. In use, strap 128 may be threaded through cinch 130 and pulled tight to apply a desired amount of pressure on the subject's lower leg. Cinch 130 may then be closed to fix strap 128 in its position. As depicted, the loose end of strap 120 may be tucked into anchor 132.

Hinge 136 may link lower strut 108 and upper strut 138 and permit rotation of lower strut 108 and upper strut 138 relative to each other. When system 101 is in position on a subject's leg, the hinge axis of hinge 136 may be parallel or substantially parallel to the hinge axis of the subject's knee in good health. It may be desirable, in some embodiments, to configure hinge 136 to have a limited and/or selectable degree of rotation (e.g., flexion and/or extension).

As depicted, upper cuff 140 may comprise anterior pad 142, anterior pad shell 144, posterior pad 146, posterior pad shell 148, thigh collar 150, and tension adjustment fastener 156. Pads 142 and/or 146 may independently comprise flexible, elastomeric, and/or resilient materials including, for example, polyurethane, polyethylene, neoprene, ethylene vinyl acetate, foam (e.g., P-Cell foam), silicone, rubber, and the like.

In some embodiments, pad shells 144 and/or 148 may independently comprise a moldable plastic, steel, a steel alloy, aluminum, an aluminum alloy, titanium, a titanium alloy, carbon fiber, an aramid fiber, a para-aramid fiber (e.g., KEVLAR), fiberglass, and combinations thereof. Pad shells 144 and/or 148 comprising a moldable material may be custom fit to a subject. A moldable plastic may include, for example, a thermoplastic (e.g., capable of more than one cycle of melting, molding, and setting) and/or a thermosetting plastic (e.g., capable of one cycle of melting, molding, and setting). Pads 142 and/or 146 may be adhered, welded, bonded, stitched, or otherwise fixed to pad shells 144 and/or 148, respectively.

Pad shells 144 and/or 148 may be fixedly attached to thigh collar 150. Thigh collar 150 may extend up to all the way around the circumference of a subject's upper leg. Thigh collar 150 may include sleeve 152 positioned, for example, at or near its midpoint. Sleeve 152 may be configured to receive strut 138. Sleeve 152 may have a cavity, the longitudinal axis of which is about perpendicular to the lengthwise axis of strut 138. Sleeve 152 may be configured to allow collar 150 to slide along the length of strut 138. Sleeve 152 may include set screw 154 positioned to adjustably contact strut 138. In use, set screw 154 may be loosened to permit collar 150 to slide along the length of strut 138. Once a desirable position is found, set screw 154 may be tightened to fix the position of collar 150 on strut 138. Set screw 154 may be positioned on the inside of collar 150 and directed outwardly toward strut 138 as shown. In some embodiments, set screw 154 may be positioned on the outside of collar 150 and directed inwardly toward strut 138. As depicted, upper cuff 140 may include three thigh collars 150. In some embodiments, more or fewer collars may be desired and/or required.

Tension adjustment fastener 156 may include strap 158, cinch 160, and anchor 162. Strap 158 maybe fixed to one end of thigh collar 150 via anchor 162. Cinch 160 may be fixed to the other end of collar 150. Cinch 160 may be configured to receive and releasably grip strap 158. In use, strap 158 may be threaded through cinch 160 and pulled tight to apply a desired amount of pressure on the subject's upper leg. Cinch 160 may then be closed to fix strap 158 in its position. As depicted, the loose end of strap 150 may be tucked into anchor 162.

Figure 2A:
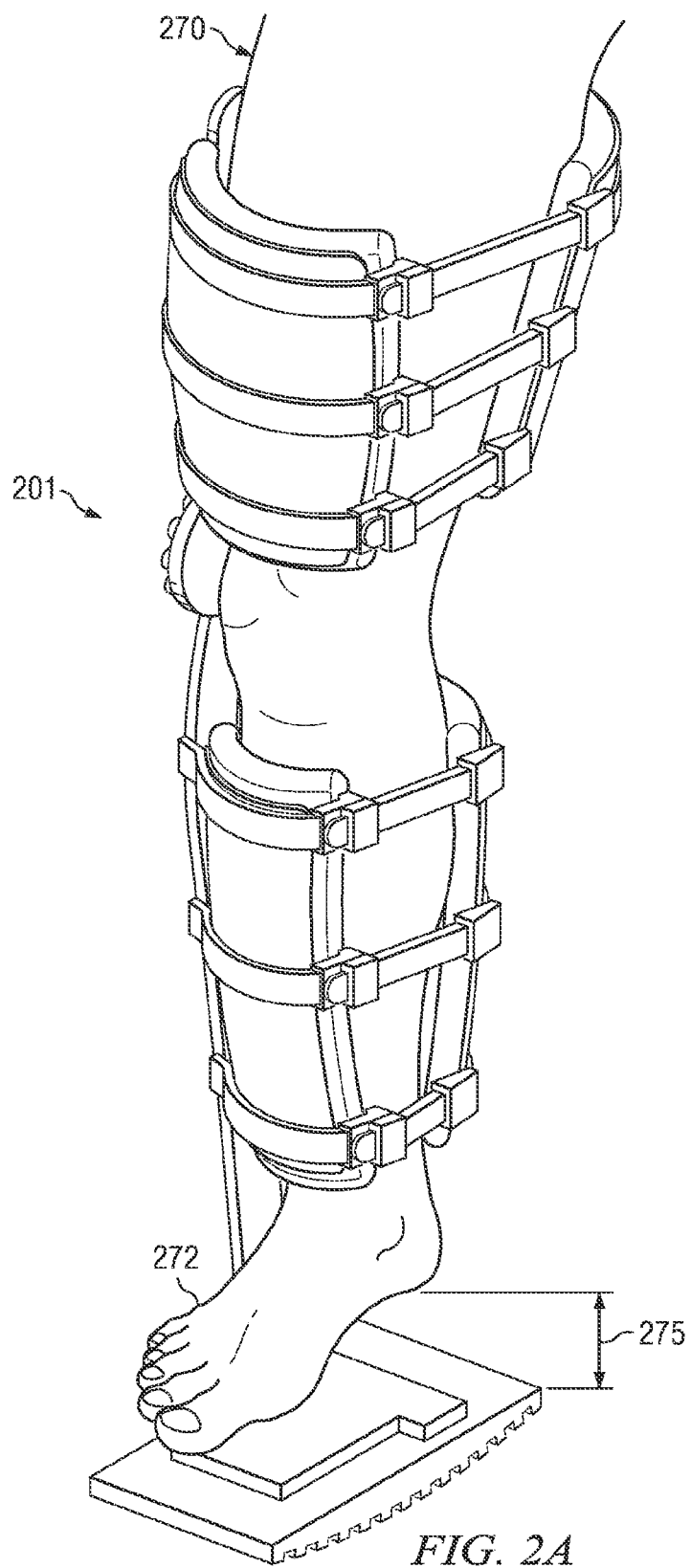
FIG. 2A illustrates a generally isometric view of a device for ambulation of a subject having an impaired lower extremity according to a specific example embodiment of the disclosure.
Figure 2B:
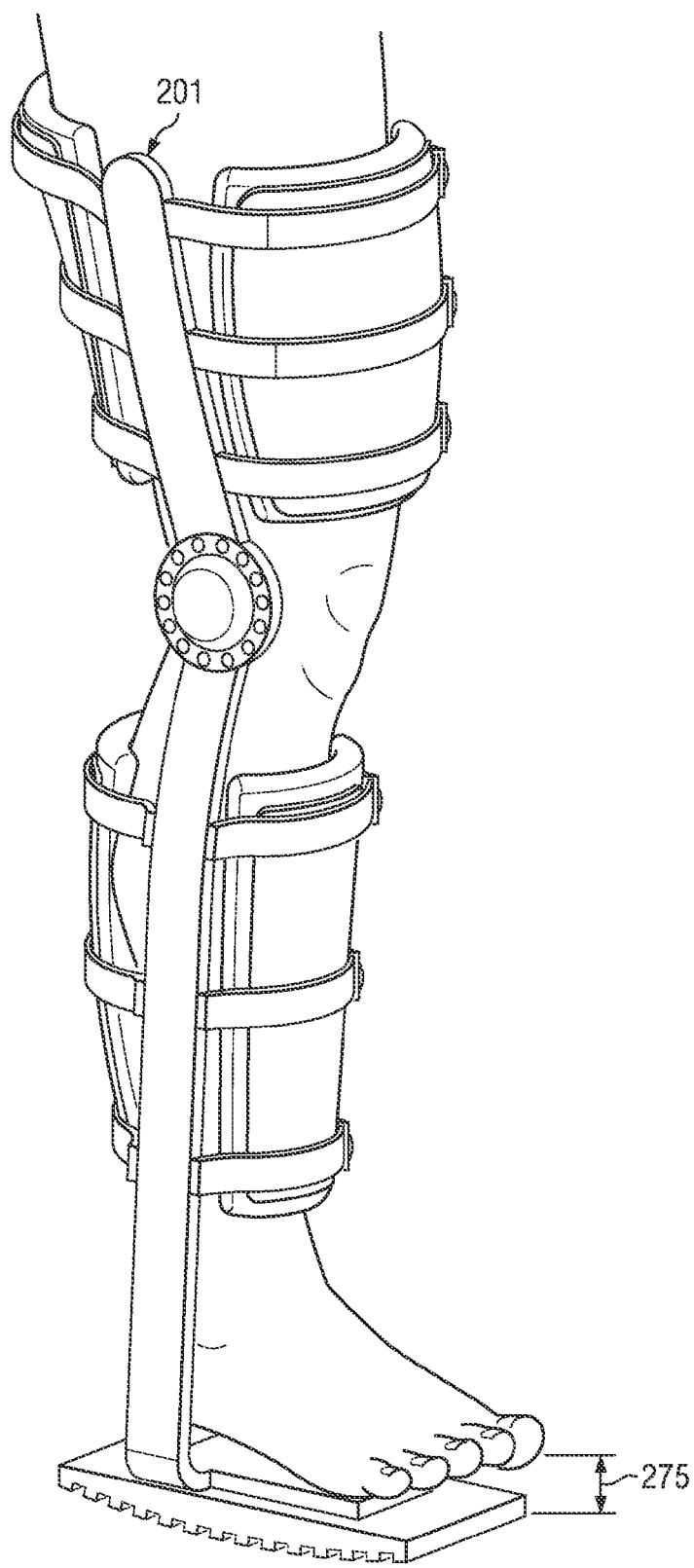
FIG. 2B illustrates a generally isometric view of a device for ambulation of a subject having an impaired lower extremity according to a specific example embodiment of the disclosure.
Figure 3A:
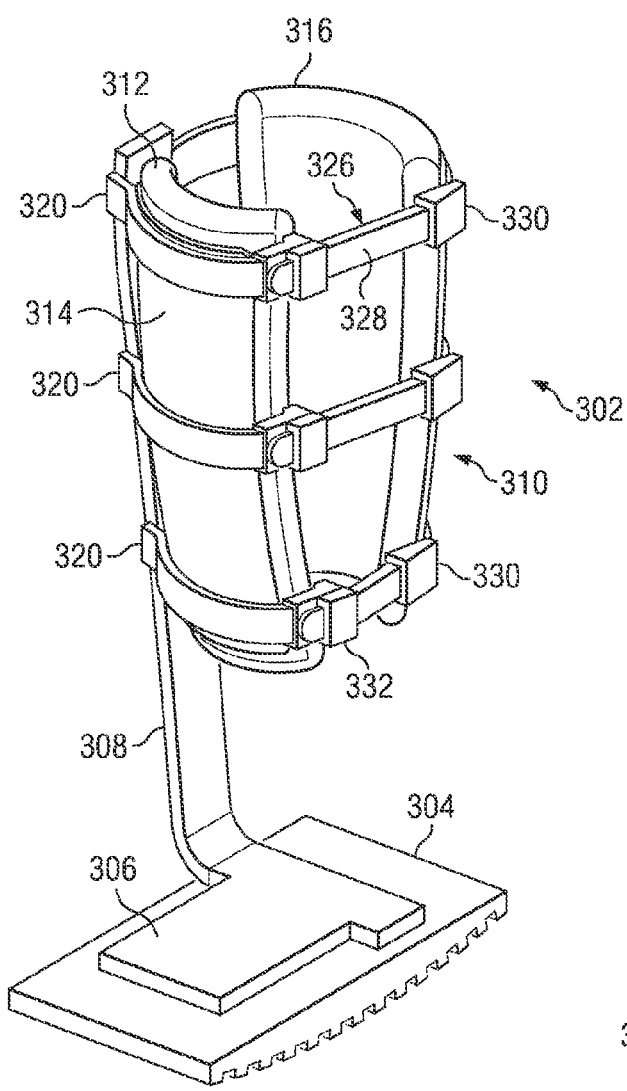
FIG. 3A illustrates a generally isometric view of a device for ambulation of a subject having an impaired lower extremity according to a specific example embodiment of the disclosure.
Figure 3B:
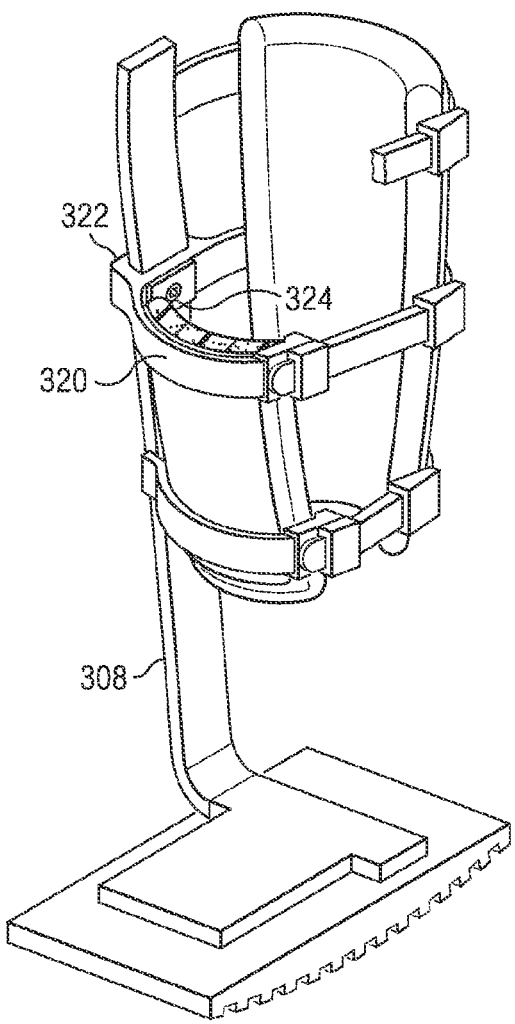
FIG. 3B illustrates a left profile view of the device for ambulation of a subject shown in FIG. 3A according to a specific example embodiment of the disclosure.
Figure 3C:
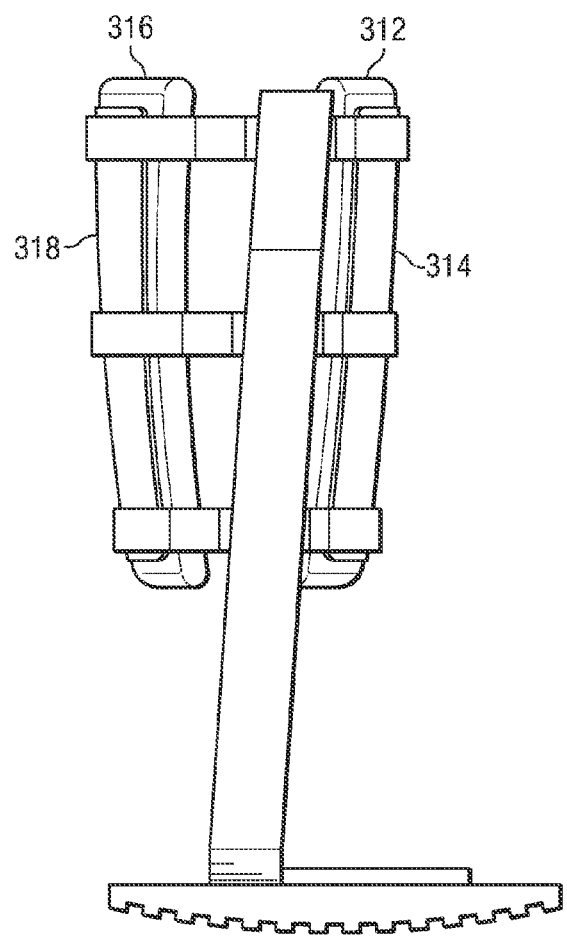
FIG. 3C illustrates a right profile view of the device for ambulation of a subject shown in FIG. 3A according to a specific example embodiment of the disclosure.
Figure 3D:
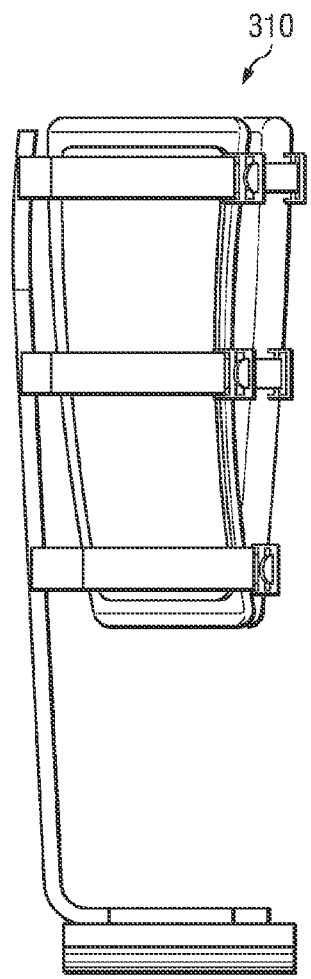
FIG. 3D illustrates a front view of the device for ambulation of a subject shown in FIG. 3A according to a specific example embodiment of the disclosure.

FIGS. 2A-2B illustrate an example load redistribution system 201 for ambulation of a subject having a lower extremity impairment, in accordance with embodiments of the present disclosure. As shown in FIGS. 2A-2B, system 201 may be configured (e.g., formed and/or adjusted) to include gap 275 between a subject's foot 272 and the higher of outsole 204 and platform 206. Gap 275 relieves subject's foot 272 and/or other lower extremities from bearing weight by diverting the load elsewhere. In some embodiments, gap 275 may be any suitable distance that avoids (e.g., minimizes, eliminates) loading foot 272 and/or other lower extremities. Gap 275 may depend, in part, upon the size and weight of the subject user. For example, a subject with a long foot may be inclined and/or compelled to support some weight on foot 272 at some points in a walking cycle (e.g., when foot 272 is at it's most rearward position). It may be desirable in such situations to adjust gap 275 to be larger. A subject, for example, a smaller subject, may desire and/or require a smaller gap 675, for example, to reduce or minimize the difference in length between the effected leg with system 602 and a healthy leg. In some embodiments, gap 275 may be from about 1 cm to about 5 cm, from about 1 cm to about 15 cm, from about 1 cm to about 10 cm, from about 1 cm to about 20 cm, from about 2 cm to about 5 cm, from about 2 cm to about 10 cm, from about 2 cm to about 15 cm, and/or from about 2 cm to about 20 cm. Gap 275 may be less than about 1 cm or more than 20 cm in some embodiments.

FIGS. 3A-3D illustrate an example of a load redistribution system 302 for ambulation of a subject having a lower extremity impairment, in accordance with embodiments of the present disclosure. As shown in FIGS. 3A-3D, load redistribution system 302 may include outsole 304, platform 306, lower strut 308, and lower cuff 310.

Outsole 304 may comprise a foot pad, the bottom of which may be rounded (e.g., rocker outsole) to facilitate walking. The bottom may be ridged as pictured or may have another tread pattern to aid ambulation. Outsole 304 may comprise a hard rubber or other suitable material. Outsole 304 may be generally rectangular in shape as depicted. Other regular and/or irregular shapes may be suitable and/or desirable in some embodiments. Platform 306 may be contiguous with strut 308 as shown or may be a separate piece fixedly attached to strut 308. The lower surface of platform 306 may be affixed to outsole 304 with any type of fastener and/or adhesive. Platform 306 may sit atop outsole 304 as shown. In some embodiments, platform 306 may be recessed within outsole 304, for example, so that the upper surface of outsole 304 is flush with the upper surface of platform 306. Platform 306 may have any regular or irregular shape. Platform 306 may be somewhat smaller than outsole 304 as depicted or may be sized to match the size of outsole 304. In some embodiments, it may be desirable for platform 306 to be larger than outsole 304. Platform 306 may comprise a rigid material suitable for bearing a subject's weight. Examples of such materials include, without limitation, steel, a steel alloy, aluminum, an aluminum alloy, titanium, a titanium alloy, carbon fiber, wood, an aramid fiber, a para-aramid fiber (e.g., KEVLAR), fiberglass, and combinations thereof.

Strut 308 may extend vertically from platform 306 to hinge to a position corresponding to or just below a subject's tibia. Strut 308 may have a lengthwise axis that is approximately parallel to the lengthwise axis of a subject's leg (e.g., lower leg). Strut 308 may comprise one or more rigid materials capable of bearing a subject's weight. Examples of such materials include, without limitation, steel, a steel alloy, aluminum, an aluminum alloy, titanium, a titanium alloy, carbon fiber, wood, an aramid fiber, a para-aramid fiber (e.g., KEVLAR), fiberglass, and combinations thereof.

As depicted, lower cuff 310 may comprise anterior pad 312, anterior pad shell 314, posterior pad 316, posterior pad shell 318, calf collar 320, and tension adjustment fastener 326. Pads 312 and/or 316 may independently comprise flexible, elastomeric, and/or resilient materials including, for example, polyurethane, polyethylene, neoprene, ethylene vinyl acetate, foam (e.g., P-Cell foam), silicone, rubber, and the like. In some embodiments, pad shells 314 and/or 318 may independently comprise a moldable plastic, steel, a steel alloy, aluminum, an aluminum alloy, titanium, a titanium alloy, carbon fiber, an aramid fiber, a para-aramid fiber (e.g., KEVLAR), fiberglass, and combinations thereof. Pad shells 314 and/or 318 comprising a moldable material may be custom fit to a subject. A moldable plastic may include, for example, a thermoplastic (e.g., capable of more than one cycle of melting, molding, and setting) and/or a thermosetting plastic (e.g., capable of one cycle of melting, molding, and setting). Pads 312 and/or 316 may be adhered, welded, bonded, stitched, or otherwise fixed to pad shells 314 and/or 318, respectively.

Pad shells 314 and/or 318 may be fixedly attached to calf collar 320. Calf collar 320 may extend up to all the way around the circumference of a subject's lower leg. Calf collar 320 may include sleeve 322 positioned, for example, at or near its midpoint. Sleeve 322 may be configured to receive strut 308. Sleeve 322 may have a cavity, the longitudinal axis of which is about perpendicular to the lengthwise axis of strut 308. Sleeve 322 may be configured to allow collar 320 to slide along the length of strut 308. Sleeve 322 may include set screw 324 positioned to adjustably contact strut 308. Each calf collar may be configured to include a sleeve and each sleeve may include a set screw. In use, set screw 324 may be loosened to permit collar 320 to slide along the length of strut 308. Once a desirable position is found, set screw 324 may be tightened to fix the position of collar 320 on strut 308. Set screw 324 may be positioned on the inside of collar 320 and directed outwardly toward strut 308 as shown. In some embodiments, set screw 324 may be positioned on the outside of collar 320 and directed inwardly toward strut 308. As depicted, lower cuff 310 may include three calf collars 320. In some embodiments, more or fewer collars may be desired and/or required.

Tension adjustment fastener 326 may include strap 328, cinch 330, and anchor 332. Strap 328 maybe fixed to one end of calf collar 320 via anchor 332. Cinch 330 may be fixed to the other end of collar 320. Cinch 330 may be configured to receive and releasably grip strap 328. In use, strap 328 may be threaded through cinch 330 and pulled tight to apply a desired amount of pressure on the subject's lower leg. Cinch 330 may then be closed to fix strap 328 in its position. As depicted, the loose end of strap 320 may be tucked into anchor 332.

Figure 4:
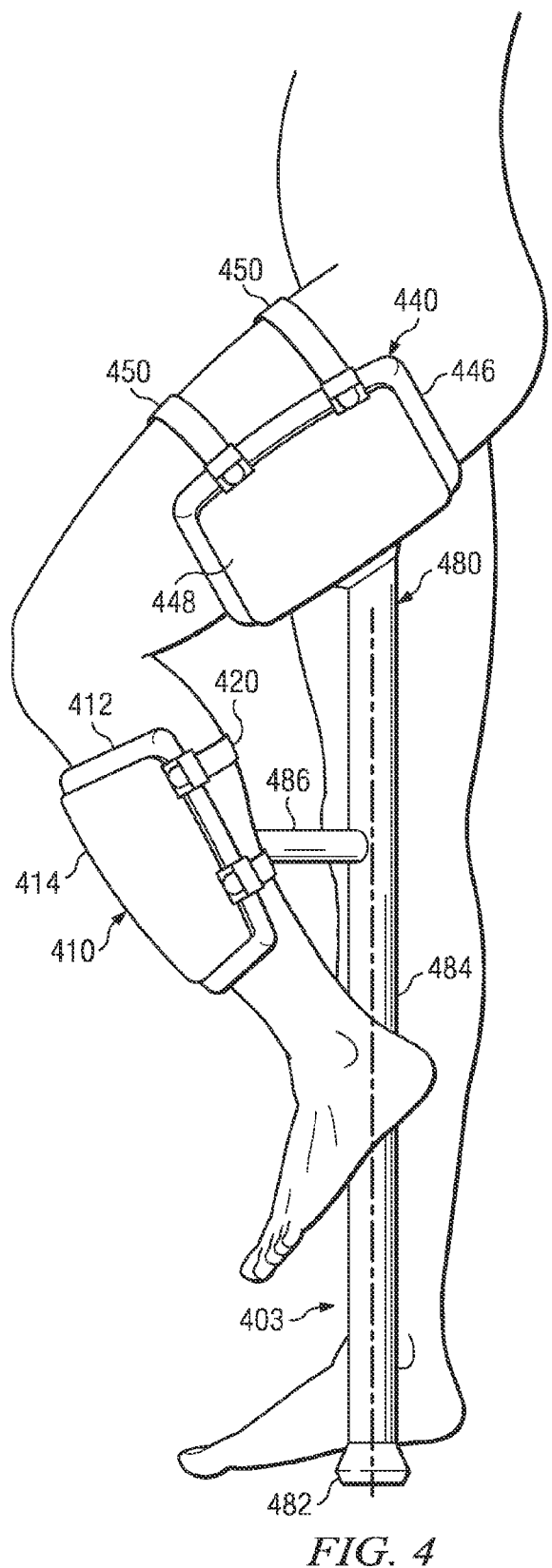
FIG. 4 illustrates a profile view of a device for ambulation of a subject having an impaired lower extremity according to a specific example embodiment of the disclosure.

FIG. 4 illustrates an example of a load redistribution system 403 for ambulation of a subject having a lower extremity impairment, in accordance with embodiments of the present disclosure. As shown in FIG. 4, load redistribution system 403 may include lower cuff 410, upper cuff 440, and rod assembly 480.

Lower cuff 410, as shown, may include anterior pad 412, anterior pad shell 414, calf collar 420, and tension adjustment fastener 426. Lower cuff 410 may be secured on a subject's lower leg in a manner similar to cuffs 110 and 310. Upper cuff 440, as shown, may include, posterior pad 446, posterior pad shell 448, calf collar 450, and tension adjustment fastener 456. Upper cuff 440 may be secured on a subject's upper leg in a manner similar to cuffs 140 and 340. Rod assembly 480, as shown, may include foot 482, vertical rod 484, and lateral bar 486.

Lateral bar 486 may be fixed to lower cuff 410 at one end and fixed to vertical rod 484 at the other as shown. In some embodiments, a lower cuff may be fixed directly to a vertical rod allowing the lateral bar to be omitted. Upper cuff 440 may be fixed directly to vertical rod 484. In some embodiments, a lateral bar may be interposed between an upper cuff and a vertical rod. Rod assembly 480 may comprise one or more rigid materials capable of bearing a subject's weight. Examples of such materials include, without limitation, steel, a steel alloy, aluminum, an aluminum alloy, titanium, a titanium alloy, carbon fiber, wood, fiberglass and combinations thereof.

Variations in the weight of a subject, the positioning of the cuff(s), and/or the dimensions of the cuff(s) may influence the pressure on a subject's leg. In some embodiments, the pressure applied by a cuff on a subject's leg may be up to about 5 psi, up to about 7.5 psi, up to about 10 psi, up to about 15 psi, up to about 20 psi, up to about 25 psi, and/or up to about 30 psi. In some embodiments, a system may include one or more sensors (e.g., pressure sensors). One or more sensors configured to detect the pressure at a particular location and/or the load born and/or or shifted.

Figure 5A:
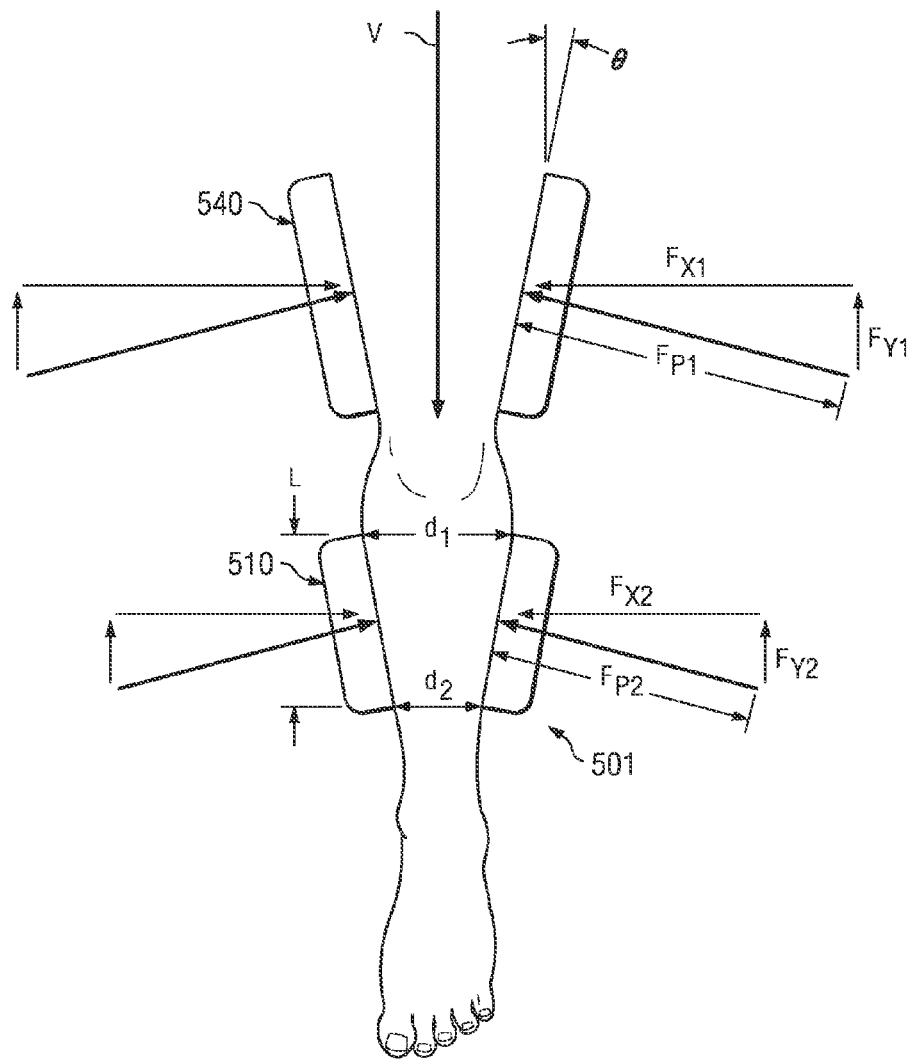
FIG. 5A illustrates a front view of a device for ambulation of a subject having an impaired lower extremity according to a specific example embodiment of the disclosure.
Figure 5B:
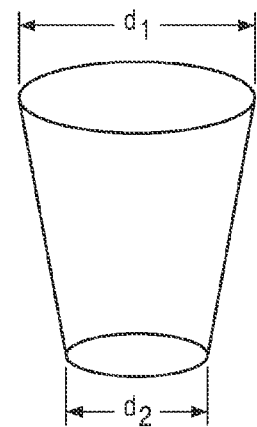
FIG. 5B illustrates a generally isometric view of a cuff according to a specific example embodiment of the disclosure.

FIGS. 5A and 5B illustrate an example of a load redistribution system 501 for ambulation of a subject having a lower extremity impairment, in accordance with embodiments of the present disclosure. As shown in FIG. 5A, load redistribution system 501 may support a subject's weight through lower strut 508 (not expressly shown), lower cuff 510 (comprising circumferential pad 511), upper strut 538 (not expressly shown), and upper cuff 540 (comprising circumferential pad 541). FIG. 5A illustrates a method for calculating the pressure to be applied to a subject's leg as system 501 bears a subject's weight. Subject's weight is represented as vector V. As depicted, pads 511 and 541 are positioned at an angle $\theta$ relative to vector V. The force applied to pad 511 is represented as vector $F_{P1}$ and the force applied to pad 511 is represented as vector $F_{P2}$. The horizontal component of vector $F_{P1}$ is represented by vector $F_{X1}$ and the vertical component is represented by vector $F_{Y1}$. The horizontal component of vector $F_{P2}$ is represented by vector $F_{X2}$ and the vertical component is represented by vector $F_{Y2}$. Since system 501 is configured to bear a subject's full weight (w), $$w = F_{Y1} + F_{Y2} \quad \text{(Equation 1)}$$

If the subject's weight (w) is distributed evenly between pads 511 and 541, $$w/2 = F_{Y1} = F_{Y2} \quad \text{(Equation 2)}$$

Thus, since $$\sin(\theta) = F_{Y1}/F_{P1} \quad \text{(Equation 3)}$$

the force $F_{P1}$ applied to a subject's leg may be calculated as follows:

$$F_{P1} = F_{Y1}/\sin(\theta) \quad \text{(Equation 4)}$$

The area of cuff 510 is given by Equation 5:

$$\text{Area} = [(d_1 + d_2)/2] * L * \pi \quad \text{(Equation 5)}$$

Thus, the pressure (P) on a subject's leg at cuff 510 is given by Equation 4:

$$P = \frac{F_{Y1}/\sin(\theta)}{[(d_1 + d_2)/2] * L * \pi} \quad \text{(Equation 6)}$$

Therefore, if pad 511 is positioned at an angle of 7° (θ), $d_1$ is 5.41 inches, $d_2$ is 3.5 inches, L is 7 inches, and the subject's weight is 180 pounds, the pressure (P) is given by $$P = \frac{(w/2)/\sin(\theta)}{[(d_1 + d_2)/2] * L * \pi} \quad \text{(Equation 7)}$$

$$P = \frac{(180/2)/\sin(7)}{[(5.41 + 3.5)/2] * 7 * \pi} \quad \text{(Equation 8)}$$

$$P = 7.5 \text{ psi}$$

FIGS. 6A-6H illustrate an example of a load redistribution system 602 for ambulation of a subject having a lower extremity impairment, in accordance with embodiments of the present disclosure. As shown in FIGS. 6A-6H, load redistribution system 602 may include outsole 604, platform 606, strut 608, support 690, and cuff 610.

Outsole 604 may comprise a foot pad, the bottom of which may be rounded (e.g., rocker outsole) to facilitate walking. The bottom may be ridged as pictured or may have another tread pattern to aid ambulation. Outsole 604 may comprise a hard rubber or other suitable material. Outsole 604 may be generally rectangular in shape as depicted. Other regular and/or irregular shapes may be suitable and/or desirable in some embodiments. Platform 606 may be contiguous with strut 608 as shown or may be a separate piece fixedly attached to strut 608. In some embodiments, outsole 604 and platform 606 may be adjustable (e.g., fore and aft) relative to each other. The lower surface of platform 606 may be affixed to outsole 604 with any type of fastener and/or adhesive. Platform 606 may sit atop outsole 604 as shown. In some embodiments, platform 606 may be recessed within outsole 604, for example, so that the upper surface of outsole 604 is flush with the upper surface of platform 606. Platform 606 may have any regular or irregular shape. Platform 606 may be somewhat smaller than outsole 604 as depicted or may be sized to match the size of outsole 604. In some embodiments, it may be desirable for platform 606 to be larger than outsole 604. Platform 606 may comprise a rigid material suitable for bearing a subject's weight. Examples of such materials include, without limitation, steel, a steel alloy, aluminum, an aluminum alloy, titanium, a titanium alloy, carbon fiber, wood, an aramid fiber, a para-aramid fiber (e.g., KEVLAR), fiberglass, and combinations thereof.

System 602 may include strut 608 positioned substantially behind a subject's leg when the leg is secured in system 602. At least a portion of strut 608 may be fixedly connected to and/or contiguous with a posterior portion of platform 606. At least a portion of strut 608 extends from a posterior portion of platform 606 in the same plane as platform 606 or a plane generally parallel to the plane of platform 606 ("horizontal" portion). At least a portion of strut 608 rises above the plane of platform 606 and generally perpendicular to the plane of platform 606 ("vertical" portion). This vertical portion may have a lengthwise axis that is approximately parallel to the lengthwise axis of a subject's leg (e.g., lower leg). Strut 608 may include bend 607 interposed between the horizontal and vertical portions of strut 608. Bend 607 may be configured to bend or curve upward from platform 606 in a manner that permits a subject a normal or generally normal stride (e.g., heel to toe contact with the ground). Strut 608 may comprise one or more rigid materials capable of bearing a subject's weight. Examples of such materials include, without limitation, steel, a steel alloy, aluminum, an aluminum alloy, titanium, a titanium alloy, carbon fiber, wood, an aramid fiber, a para-aramid fiber (e.g., KEVLAR), fiberglass, and combinations thereof While strut 608 may be rigid to support a subject's weight, some resilience/flexibility may be tolerated and/or desirable in some embodiments.

As depicted, cuff 610 may comprise anterior pad 612, anterior pad shell 614, posterior pad 616, posterior pad shell 618, and tension adjustment fastener 626. Pad 612 may include one or more apertures 613. Shell 614 may include one or more apertures 615. Pad 616 may include one or more apertures 617. Shell 618 may include one or more apertures 619. Pad apertures 613 and 617 may be independently aligned (e.g., partially or completely) with shell apertures 615 and 619, respectively. Pads 612 and/or 616 may independently comprise flexible, elastomeric, and/or resilient materials including, for example, polyurethane, polyethylene, neoprene, ethylene vinyl acetate, foam (e.g., P-Cell foam), silicone, rubber, and the like. Pad shells 614 and/or 618 may independently comprise a moldable plastic. In some embodiments, pad shells 614 and/or 618 may independently comprise steel, a steel alloy, aluminum, an aluminum alloy, titanium, a titanium alloy, carbon fiber, an aramid fiber, a para-aramid fiber (e.g., KEVLAR), fiberglass, and combinations thereof. Pad shells 614 and/or 618 comprising a moldable material may be custom fit to a subject. A moldable plastic may include, for example, a thermoplastic (e.g., capable of more than one cycle of melting, molding, and setting) and/or a thermosetting plastic (e.g., capable of one cycle of melting, molding, and setting). Pads 612 and/or 616 may be adhered, welded, bonded, stitched, or otherwise fixed to pad shells 614 and/or 618, respectively.

Figure 6A:
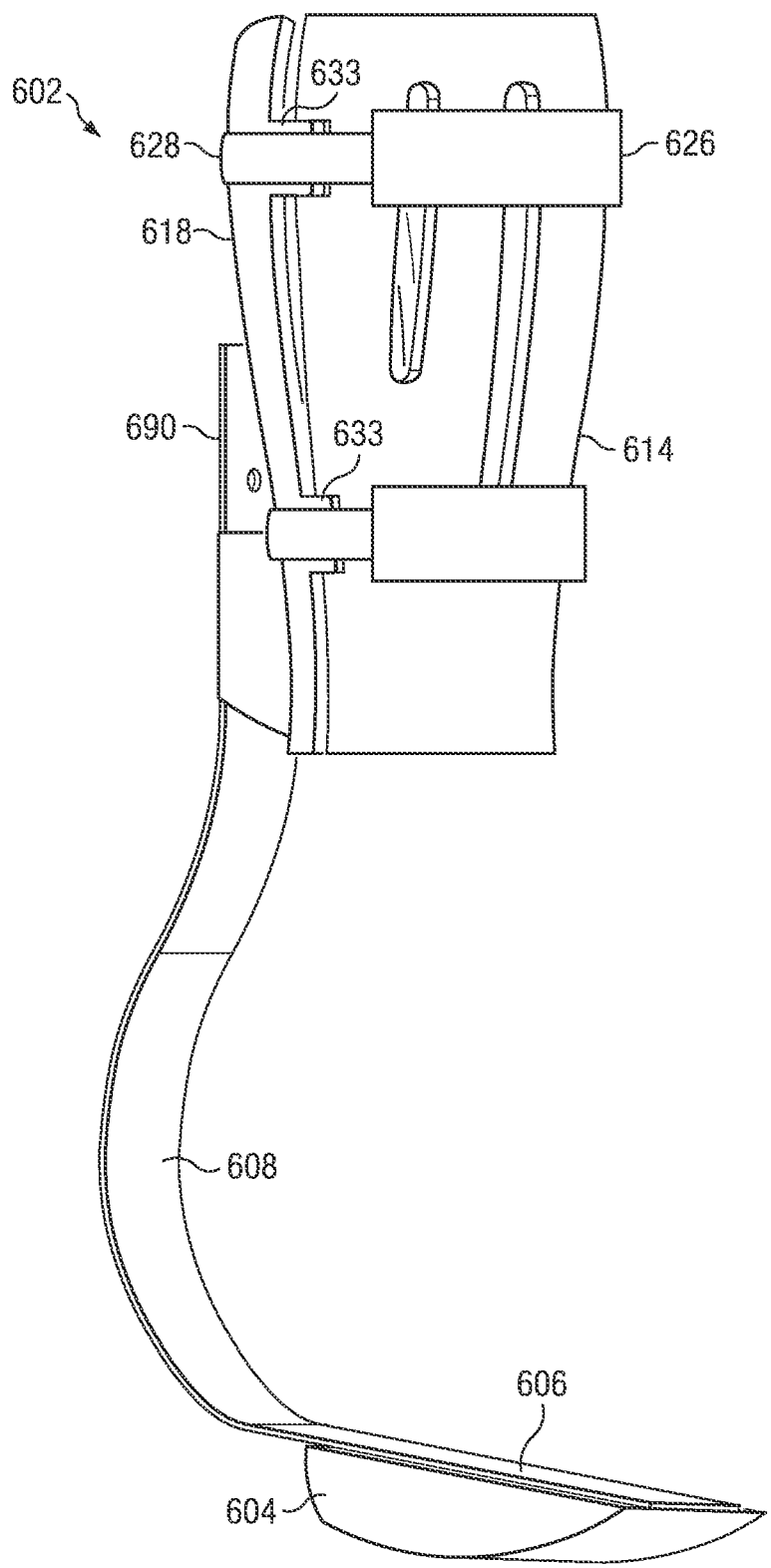
FIG. 6A illustrates a generally isometric view of a device for ambulation of a subject having an impaired lower extremity according to a specific example embodiment of the disclosure.
Figure 6B:
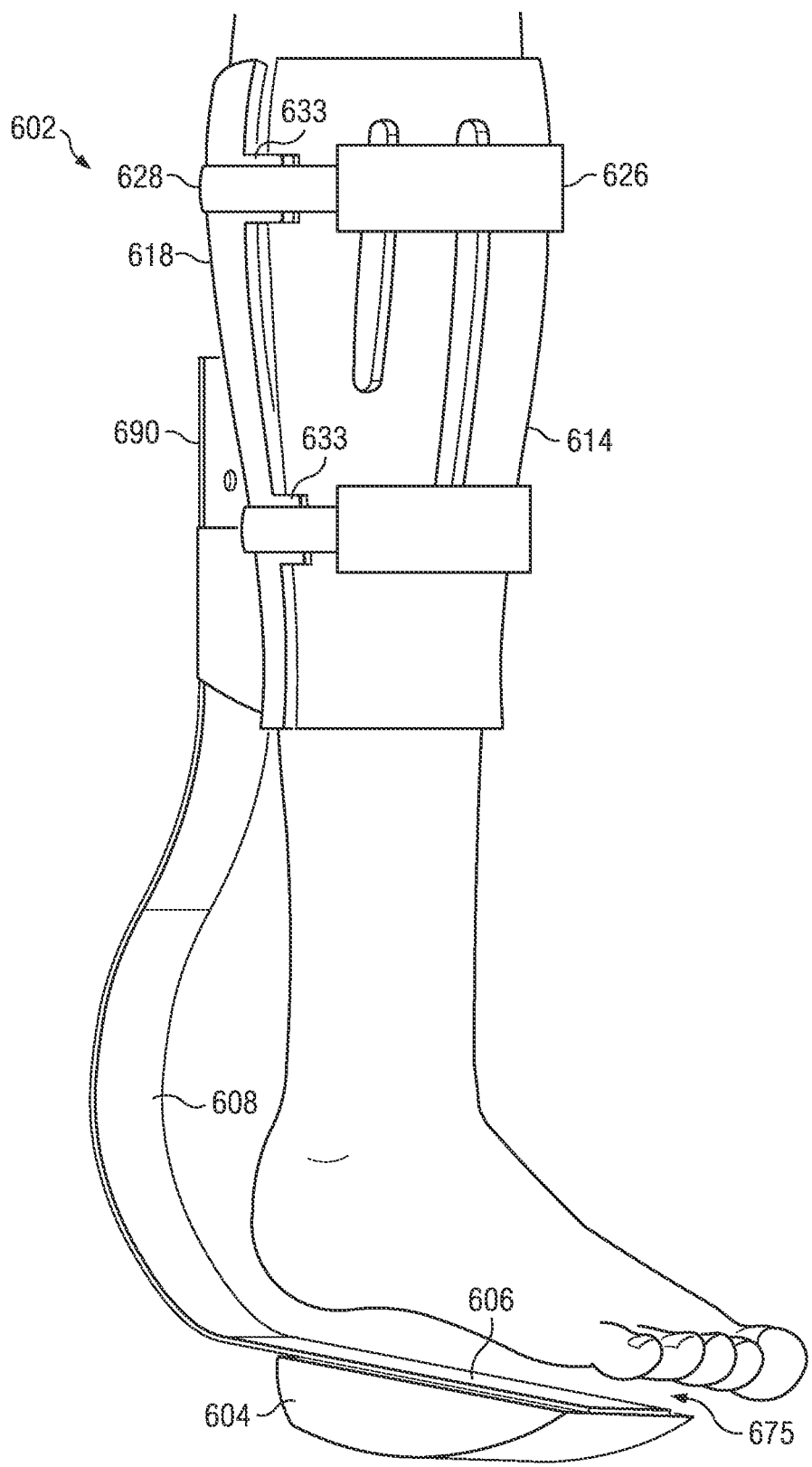
FIG. 6B illustrates a generally isometric view of the device for ambulation of a subject shown in FIG. 6A according to a specific example embodiment of the disclosure.
Figure 6C:
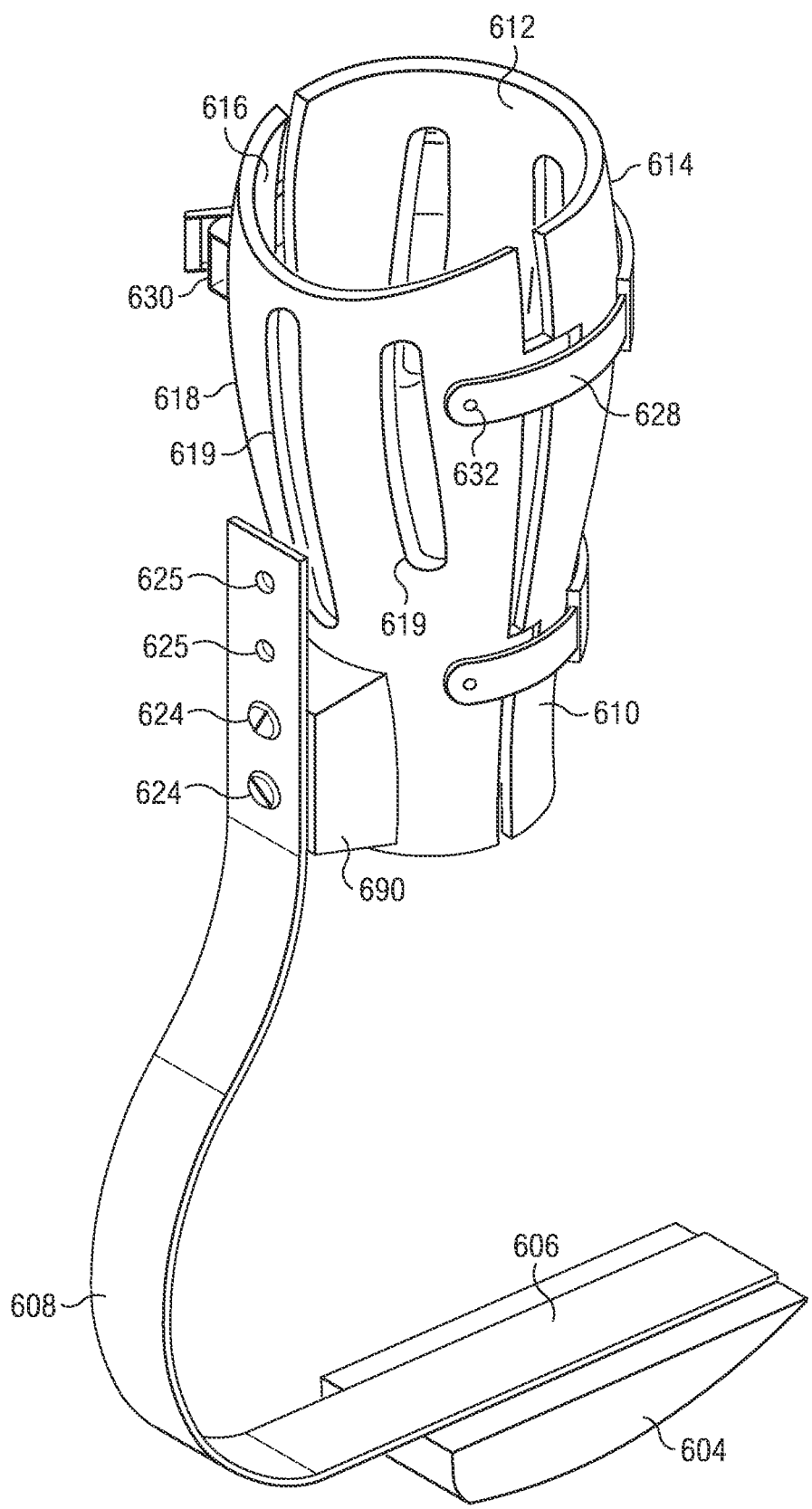
FIG. 6C illustrates a generally isometric view of the device for ambulation of a subject shown in FIG. 6A according to a specific example embodiment of the disclosure.
Figure 6D:
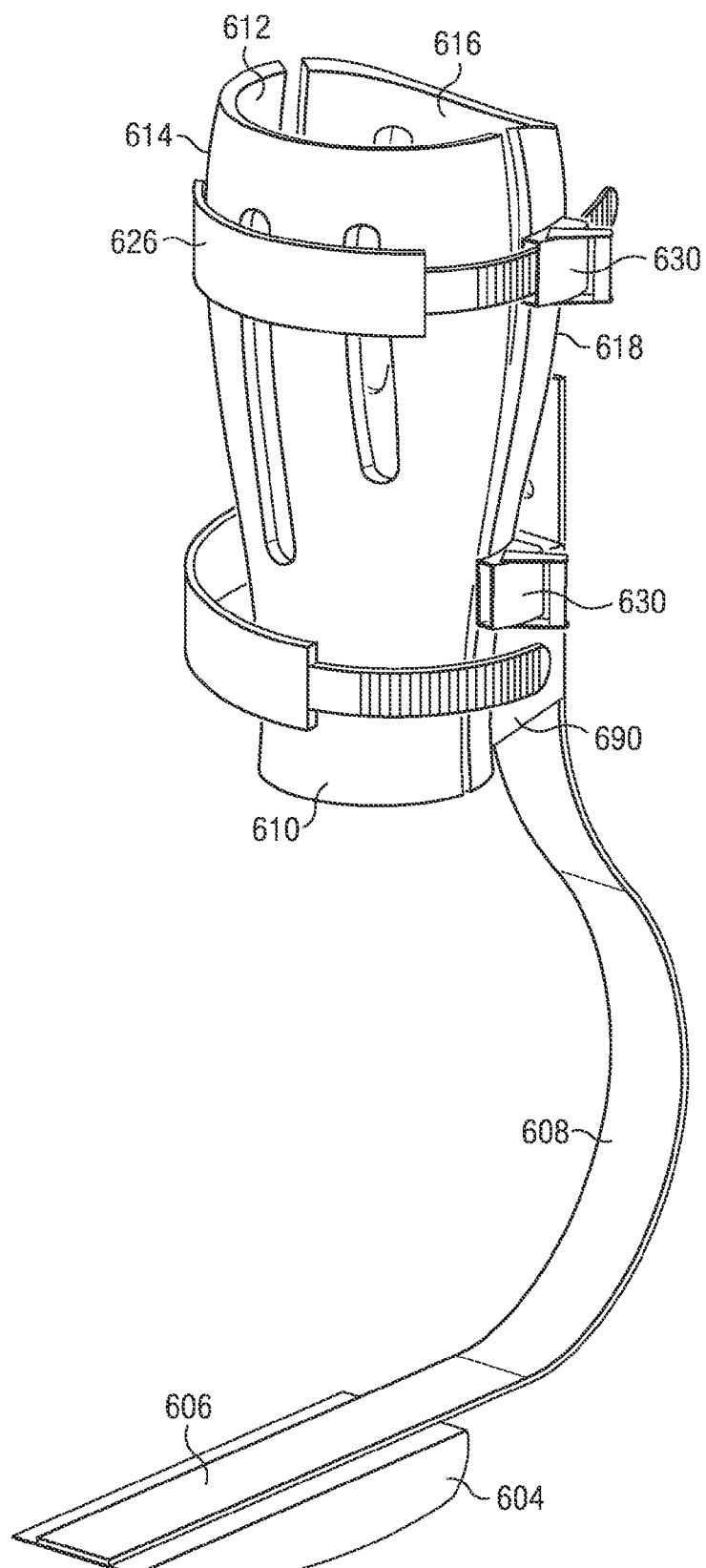
FIG. 6D illustrates a generally isometric view of the device for ambulation of a subject shown in FIG. 6A according to a specific example embodiment of the disclosure.
Figure 6E:
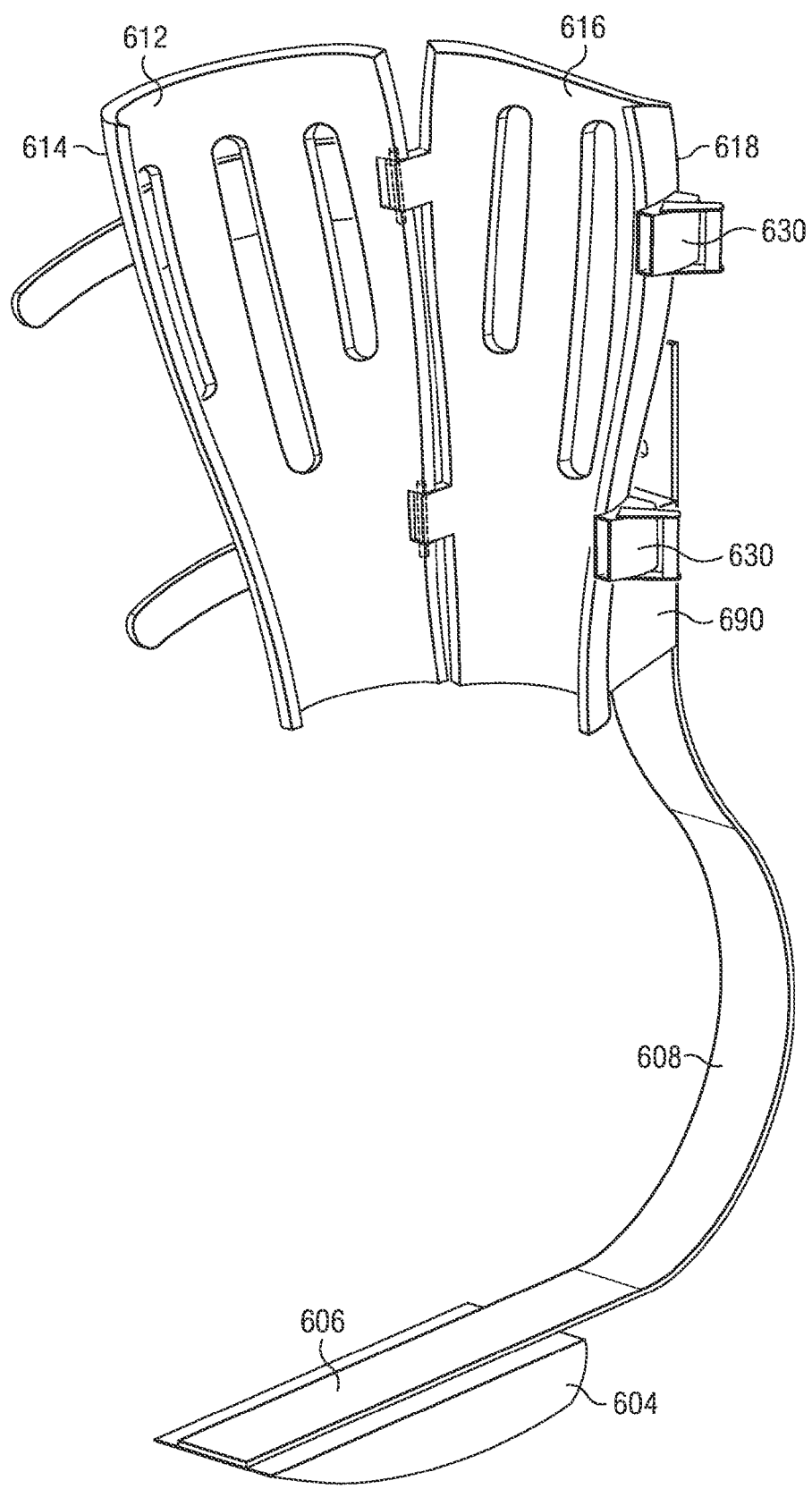
FIG. 6E illustrates a generally isometric view of the device for ambulation of a subject shown in FIG. 6A according to a specific example embodiment of the disclosure.
Figure 6F:
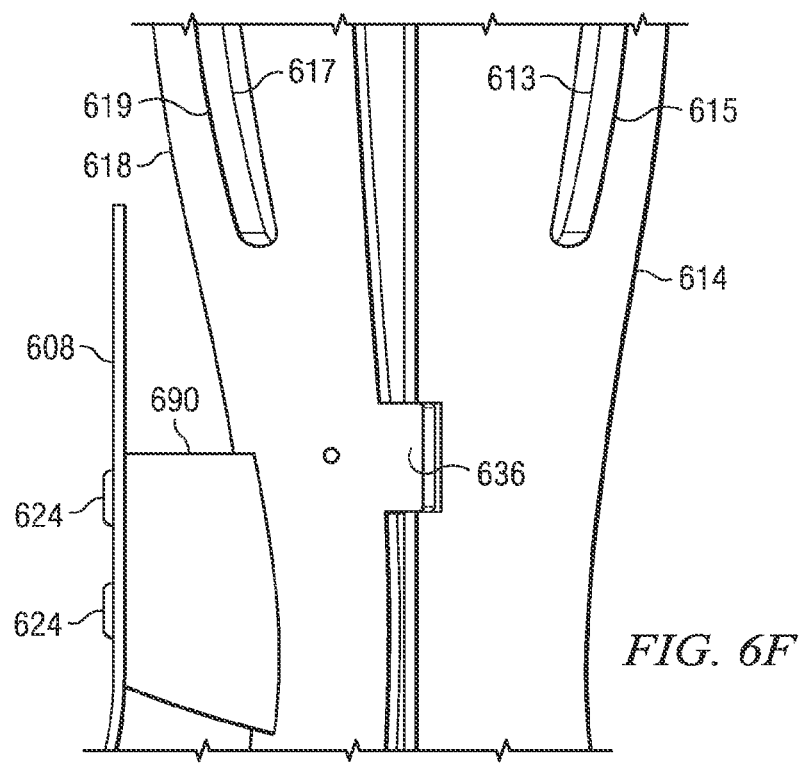
FIG. 6F illustrates a right profile view of the device for ambulation of a subject shown in FIG. 6A according to a specific example embodiment of the disclosure.
Figure 6G:
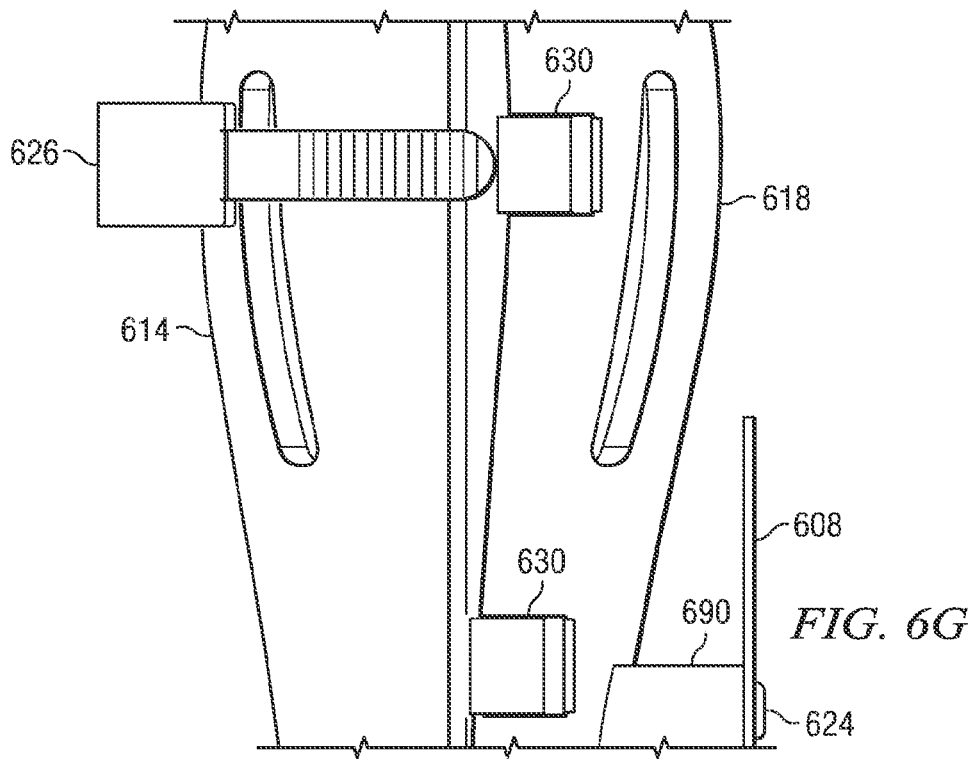
FIG. 6G illustrates a left profile view of the device for ambulation of a subject shown in FIG. 6A according to a specific example embodiment of the disclosure.
Figure 6H:
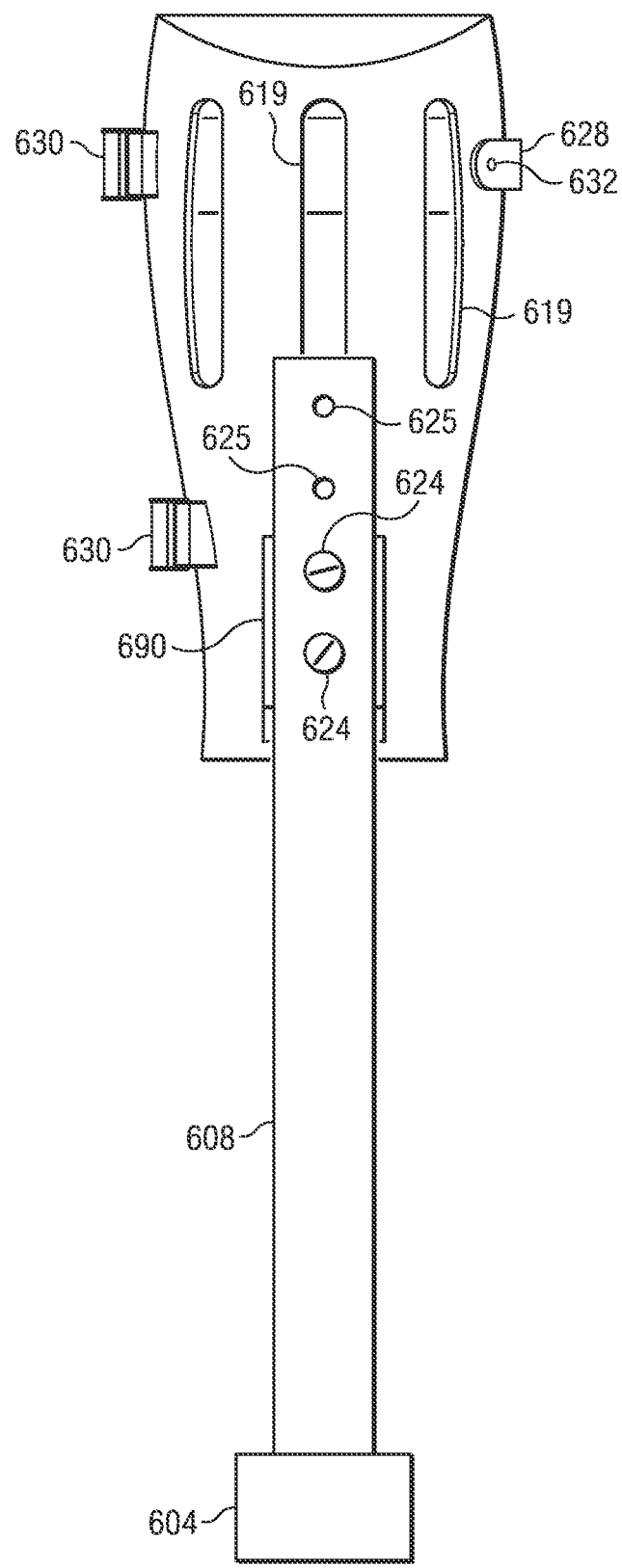
FIG. 6H illustrates a rear view of the device for ambulation of a subject shown in FIG. 6A according to a specific example embodiment of the disclosure.

As shown in FIG. 6C, pad shell 618 may be fixedly attached to support 690. Pad shells 614 and 618 may be attached to each other through one or more hinges 633. Support 690 may be attached to strut 608—one or more screws 624 may be secured to support 690 through one or more holes 625 in strut 608. As shown in FIG. 6C, a plurality of holes 625 along a vertical axis of strut 608 affords a health care worker and/or a subject the opportunity to adjust the height of cuff 610.

Tension adjustment fastener 626 may include strap 628, cinch 630, and anchor 632. Strap 628 maybe fixed to posterior pad shell 618 via anchor 632. Cinch 630 may be fixed to posterior pad shell 618 at a point along the circumference of shell 618 and spaced away from anchor 632. Cinch 630 may be configured to receive and releasably grip strap 628. In use, strap 628 may be threaded through cinch 630 and pulled tight to apply a desired amount of pressure on the subject's lower leg. Cinch 630 may then be closed to fix strap 628 in its position. System 602 may include one, two (pictured), three or more tension adjustment fasteners 626.

FIG. 6B illustrates an example load redistribution system 602 for ambulation of a subject having a lower extremity impairment, in accordance with embodiments of the present disclosure. As shown in FIG. 6B, system 602 may be configured (e.g., formed and/or adjusted) to include gap 675 between a subject's foot 672 and the higher of outsole 604 and platform 606. Gap 675 relieves subject's foot 672 and/or other lower extremities from bearing weight by diverting at least a portion of the load elsewhere (e.g., all or substantially all of the load). In some embodiments, gap 675 may be any suitable distance that avoids (e.g., minimizes, eliminates)

loading foot 672 and/or other lower extremities. The extent of gap 675 may depend, in part, upon the size and weight of the subject user. For example, a subject with a long foot may be inclined and/or compelled to support some weight on foot 672 at some points in a walking cycle (e.g., when foot 672 is at it's most rearward position with the toes nearest the ground and the heal elevated). It may be desirable in such situations to adjust gap 675 to be larger. A subject, for example, a smaller subject, may desire and/or require a smaller gap 675, for example, to reduce or minimize the difference in length between the effected leg with system 602 and a healthy leg. In some embodiments, gap 675 may be from about 1 cm to about 5 cm, from about 1 cm to about 15 cm, from about 1 cm to about 10 cm, from about 1 cm to about 20 cm, from about 2 cm to about 5 cm, from about 2 cm to about 10 cm, from about 2 cm to about 15 cm, and/or from about 2 cm to about 20 cm. Gap 675 may be less than about 1 cm or more than 20 cm in some embodiments.

FIGS. 7A-7H illustrate an example of a load redistribution system 702 for ambulation of a subject having a lower extremity impairment, in accordance with embodiments of the present disclosure. As shown in FIGS. 7A-7H, load redistribution system 702 may include outsole 704, pad 705, platform 706, strut 708, support 791, and cuff 710.

Outsole 704 may comprise a foot pad, the bottom of which may be rounded (e.g., rocker outsole) to facilitate walking. The bottom may be ridged as pictured or may have another tread pattern to aid ambulation. Outsole 704 may comprise a hard rubber or other suitable material. Outsole 704 may have any regular or irregular shape. For example, outsole 704 may be configured to resemble the tread of a running shoe, a dress shoe, and/or a boot. As depicted, outsole 704 may include a flange that extends from the plane of the walking surface in a generally vertical direction along the back of strut 708. This flange may facilitate traction and/or a normal or improved stride. Other regular and/or irregular shapes may be suitable and/or desirable in some embodiments. Platform 706 may be contiguous with strut 708 as shown or may be a separate piece fixedly attached to strut 708. In some embodiments, outsole 704 and platform 706 may be adjustable (e.g., fore and aft) relative to each other. The lower surface of platform 706 may be affixed to outsole 704 with any type of fastener and/or adhesive. Platform 706 may sit atop outsole 704 as shown. In some embodiments, platform 706 may be recessed within outsole 704, for example, so that the upper surface of outsole 704 is flush with the upper surface of platform 706. Platform 706 may have any regular or irregular shape. Platform 706 may be somewhat smaller than outsole 704 as depicted or may be sized to match the size of outsole 704. In some embodiments, it may be desirable for platform 706 to be larger than outsole 704. Platform 706 may comprise a rigid material suitable for bearing a subject's weight. Examples of such materials include, without limitation, steel, a steel alloy, aluminum, an aluminum alloy, titanium, a titanium alloy, carbon fiber, wood, an aramid fiber, a para-aramid fiber (e.g., KEVLAR), fiberglass, and combinations thereof.

System 702 may include strut 708 positioned substantially behind a subject's leg when the leg is secured in system 702. At least a portion of strut 708 may be fixedly connected to and/or contiguous with a posterior portion of platform 706. Strut 708 may have an S-shaped profile as shown in FIG. 7C or it may form and "L" with platform 706 (not expressly illustrated). At least a portion of strut 708 extends from a posterior portion of platform 706 in the same plane as platform 706 or a plane generally parallel to the plane of platform 706 ("horizontal" portion). At least a portion of strut 708 rises above the plane of platform 706 and generally perpendicular to the plane of platform 706 ("vertical" portion). This vertical portion may have a lengthwise axis that is approximately parallel to the lengthwise axis of a subject's leg (e.g., lower leg). Strut 708 may include bend 707 interposed between the horizontal and vertical portions of strut 708. Bend 707 may be configured to bend or curve upward from platform 706 in a manner that permits a subject a normal or generally normal stride (e.g., heel to toe contact with the ground). Strut 708 may comprise one or more rigid materials capable of bearing a subject's weight. Examples of such materials include, without limitation, steel, a steel alloy, aluminum, an aluminum alloy, titanium, a titanium alloy, carbon fiber, wood, an aramid fiber, a para-aramid fiber (e.g., KEVLAR), fiberglass, and combinations thereof While strut 708 may be rigid to support a subject's weight, some resilience/flexibility may be tolerated and/or desirable in some embodiments.

As depicted, cuff 710 may comprise anterior bladder 712, anterior shell 714, posterior bladder 716, posterior shell 718, and tension adjustment fastener 726. Bladder 712 may include one or more protrusions 713. Shell 714 may include one or more apertures 715. Bladder 716 may include one or more protrusions 717. Shell 718 may include one or more apertures 719. Bladder protrusions 713 and 717 may be aligned with shell apertures 715 and 719, respectively to reduce or prevent, for example, movement of bladders relative to shells. Bladders 712 and/or 716 may independently comprise flexible, elastomeric, and/or resilient materials including, for example, polyurethane, polyethylene, neoprene, ethylene vinyl acetate, foam (e.g., P-Cell foam), silicone, rubber, and the like. Each bladder may have an inlet (712a and/or 716a) and an outlet (712b and/or 716b). System 702 may be custom fit to a subject by mounting system 702 on the subject and subsequently injecting a fill material into a bladder inlet (712a and/or 716a). Fill material may be injected in some embodiment until it begins to be released from bladder outlet (712b and/or 716b). In some embodiments, a fill material may be flowable (e.g., a liquid) when it enters a bladder. A fill material may later convert and/or be converted to a resilient, semi-resilient, or non-resilient gel or non-liquid (e.g., solid) material. Examples of fill materials include, for example, foam, spray foam, gel foam, and/or combinations thereof.

Shells 714 and/or 718 may independently comprise a moldable plastic. In some embodiments, shells 714 and/or 718 may independently comprise steel, a steel alloy, aluminum, an aluminum alloy, titanium, a titanium alloy, carbon fiber, an aramid fiber, a para-aramid fiber (e.g., KEVLAR), fiberglass, and combinations thereof. Shells 714 and/or 718 comprising a moldable material may be custom fit to a subject. A moldable plastic may include, for example, a thermoplastic (e.g., capable of more than one cycle of melting, molding, and setting) and/or a thermosetting plastic (e.g., capable of one cycle of melting, molding, and setting). Bladders 712 and/or 716 may be adhered, welded, bonded, stitched, or otherwise fixed to shells 714 and/or 718, respectively.

Figure 7A:
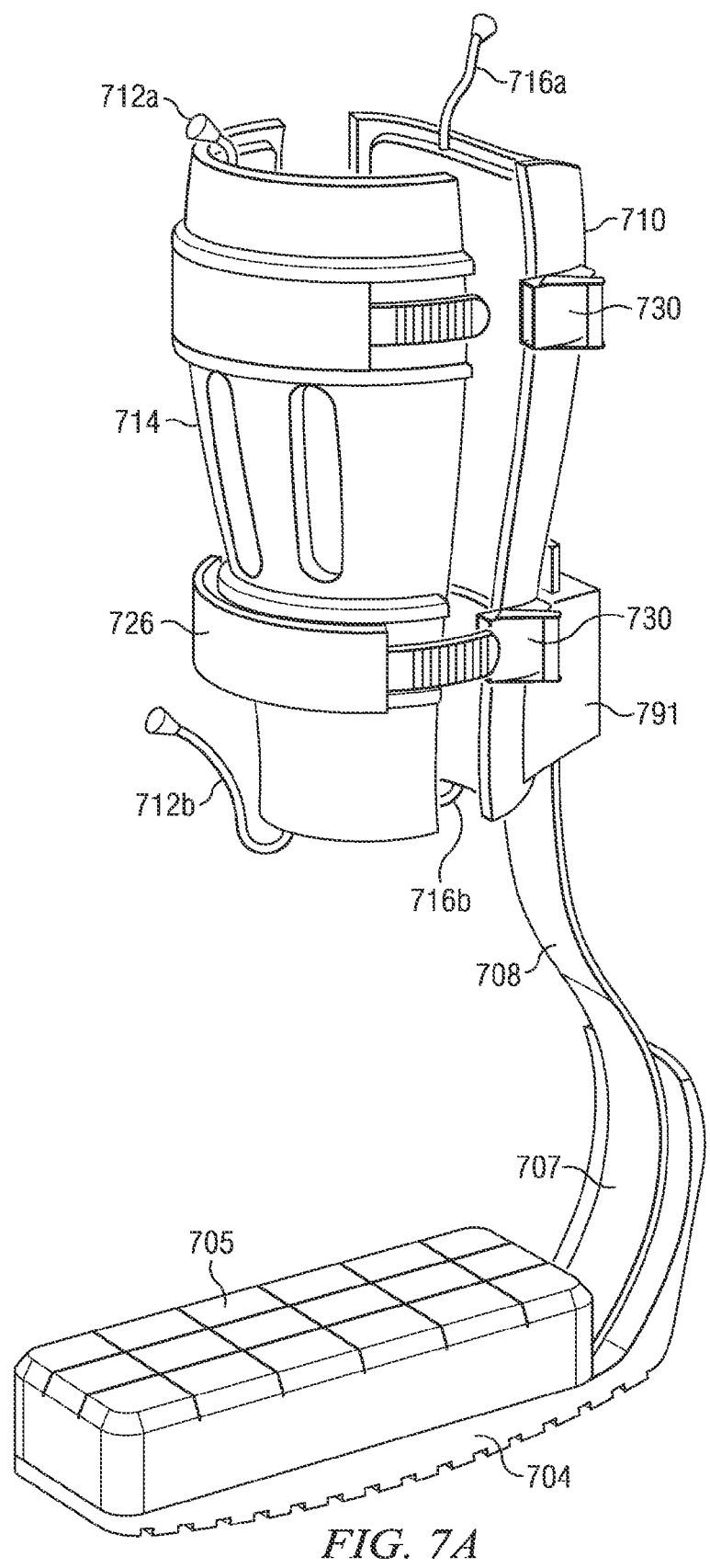
FIG. 7A illustrates a generally isometric view of a device for ambulation of a subject having an impaired lower extremity according to a specific example embodiment of the disclosure.
Figure 7B:
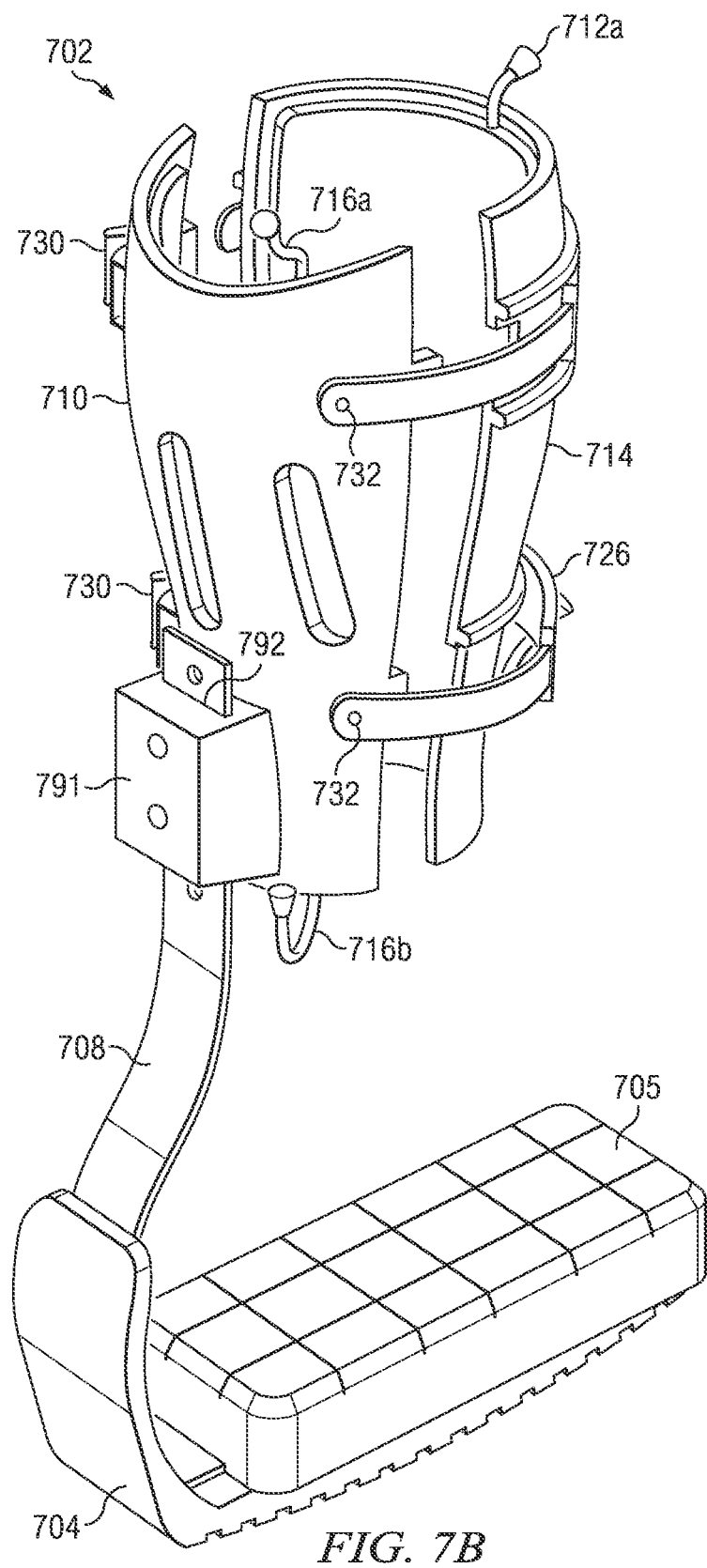
FIG. 7B illustrates a generally isometric view of the device for ambulation of a subject shown in FIG. 7A according to a specific example embodiment of the disclosure.
Figure 7C:
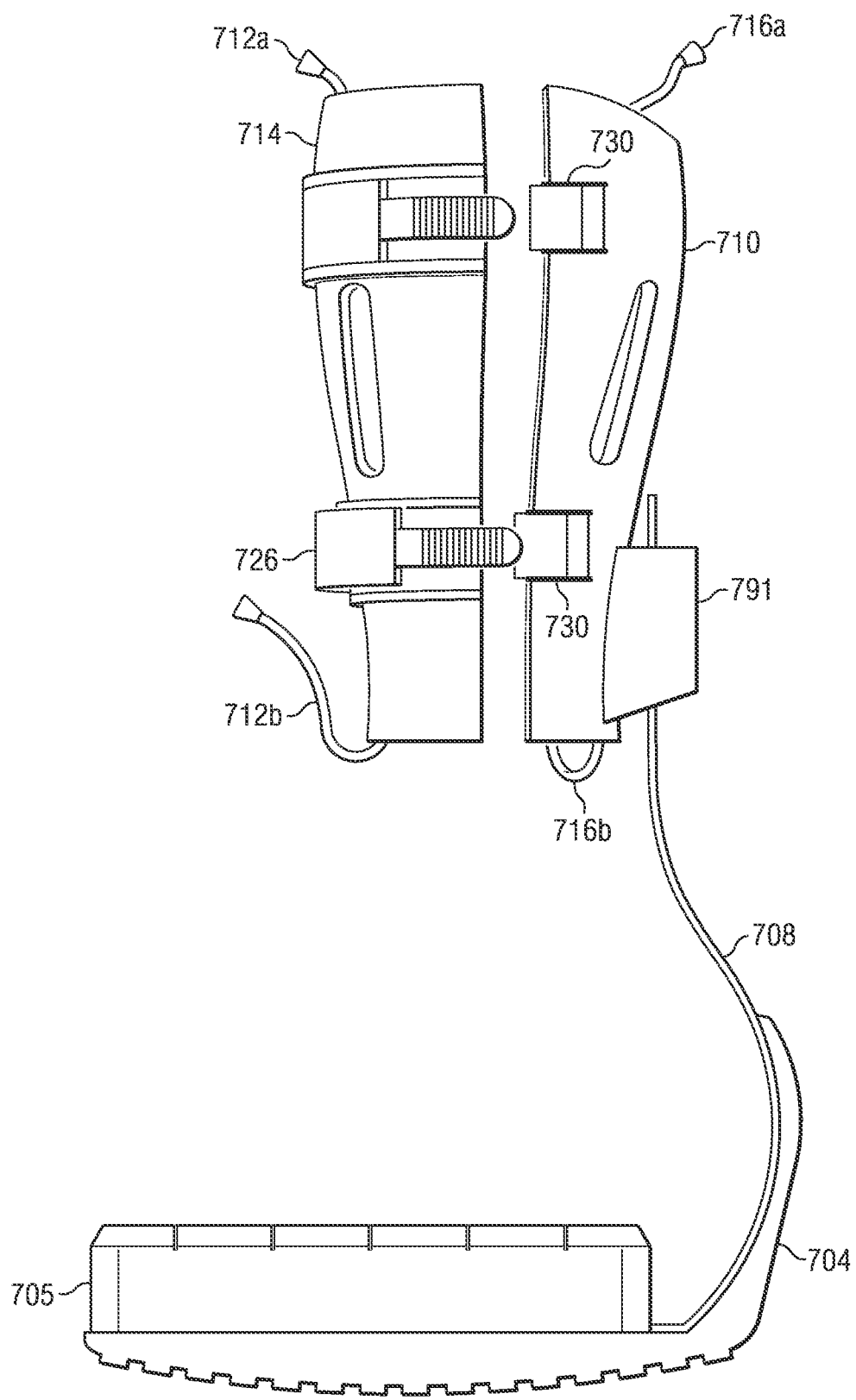
FIG. 7C illustrates a left profile view of the device for ambulation of a subject shown in FIG. 7A according to a specific example embodiment of the disclosure.

As shown in FIG. 7B, shell 718 may be fixedly attached to support 791. Support 791 may be attached to strut 708—one or more screws 724 may be secured to support 791 through one or more holes 725 in strut 708. As shown in FIG. 7B, a plurality of holes 725 along a vertical axis of strut 708 affords a health care worker and/or a subject the opportunity to adjust the height of cuff 710.

Tension adjustment fastener 726 may include strap 728, cinch 730, and anchor 732. Strap 728 may be fixed to posterior shell 718 via anchor 732. Cinch 730 may be fixed to posterior shell 718 at a point along the circumference of shell 718 and spaced away from anchor 732. Cinch 730 may be configured to receive and releasably grip strap 728. In use, strap 728 may be threaded through cinch 730 and pulled tight to apply a desired amount of pressure on the subject's lower leg. Cinch 730 may then be closed to fix strap 728 in its position. System 702 may include one, two (pictured), three or more tension adjustment fasteners 726.

Figure 7D:
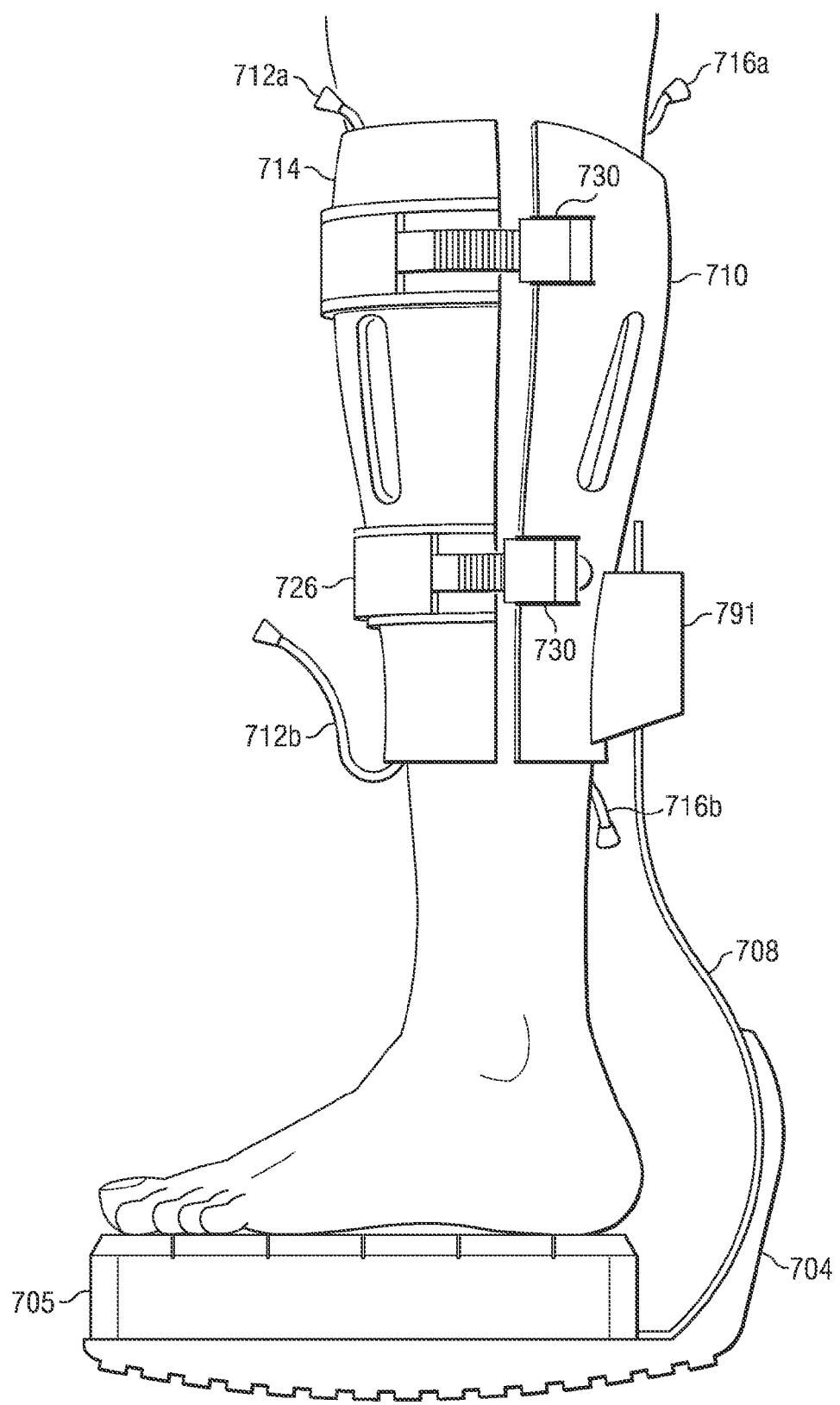
FIG. 7D illustrates a left profile view of the device for ambulation of a subject shown in FIG. 7A according to a specific example embodiment of the disclosure.
Figure 7E:
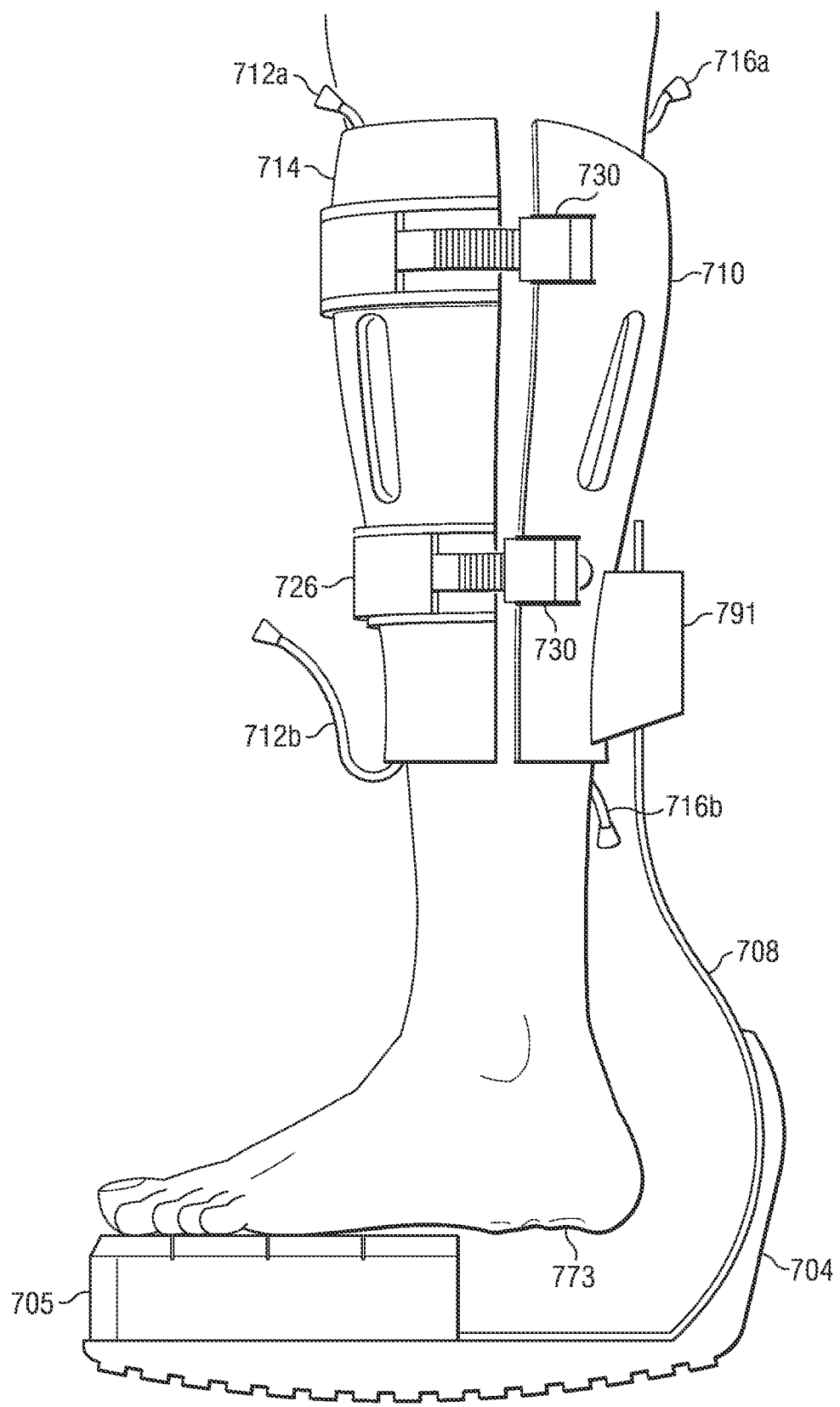
FIG. 7E illustrates a left profile view of the device for ambulation of a subject shown in FIG. 7A according to a specific example embodiment of the disclosure.

FIGS. 7D and 7E illustrate an example load redistribution system 702 for ambulation of a subject having a lower extremity impairment, in accordance with embodiments of the present disclosure. As shown in FIG. 7D, system 702 may include pad 705 positioned to apply just enough pressure to the bottom of a subject's foot (e.g., the toes and/or the ball of the foot) to hold it generally perpendicular to the long axis of the lower leg (e.g., tibia and/or fibula). As shown in FIG. 7E, one or more segments of pad 705 may be removed to accommodate the particular desires or needs of a subject with ulcer 773 or other foot injury. Pad 705 may span up to the entire gap 775. Pad 705 may comprise flexible, elastomeric, and/or resilient materials including, for example, polyurethane, polyethylene, neoprene, ethylene vinyl acetate, foam (e.g., P-Cell foam), silicone, rubber, and the like.

Figure 7F:
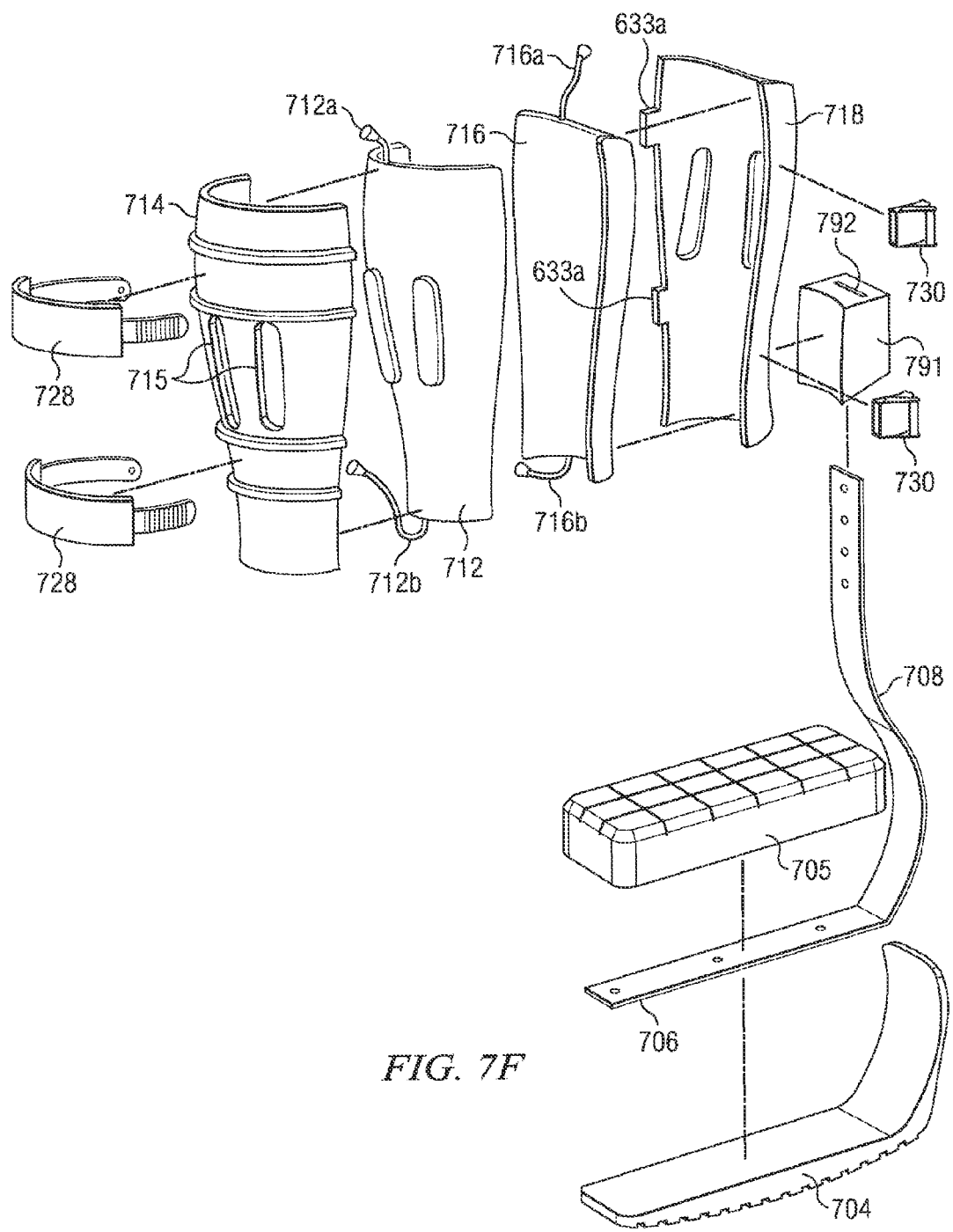
FIG. 7F illustrates an exploded view of the device for ambulation of a subject shown in FIG. 7A according to a specific example embodiment of the disclosure.
Figure 7G:
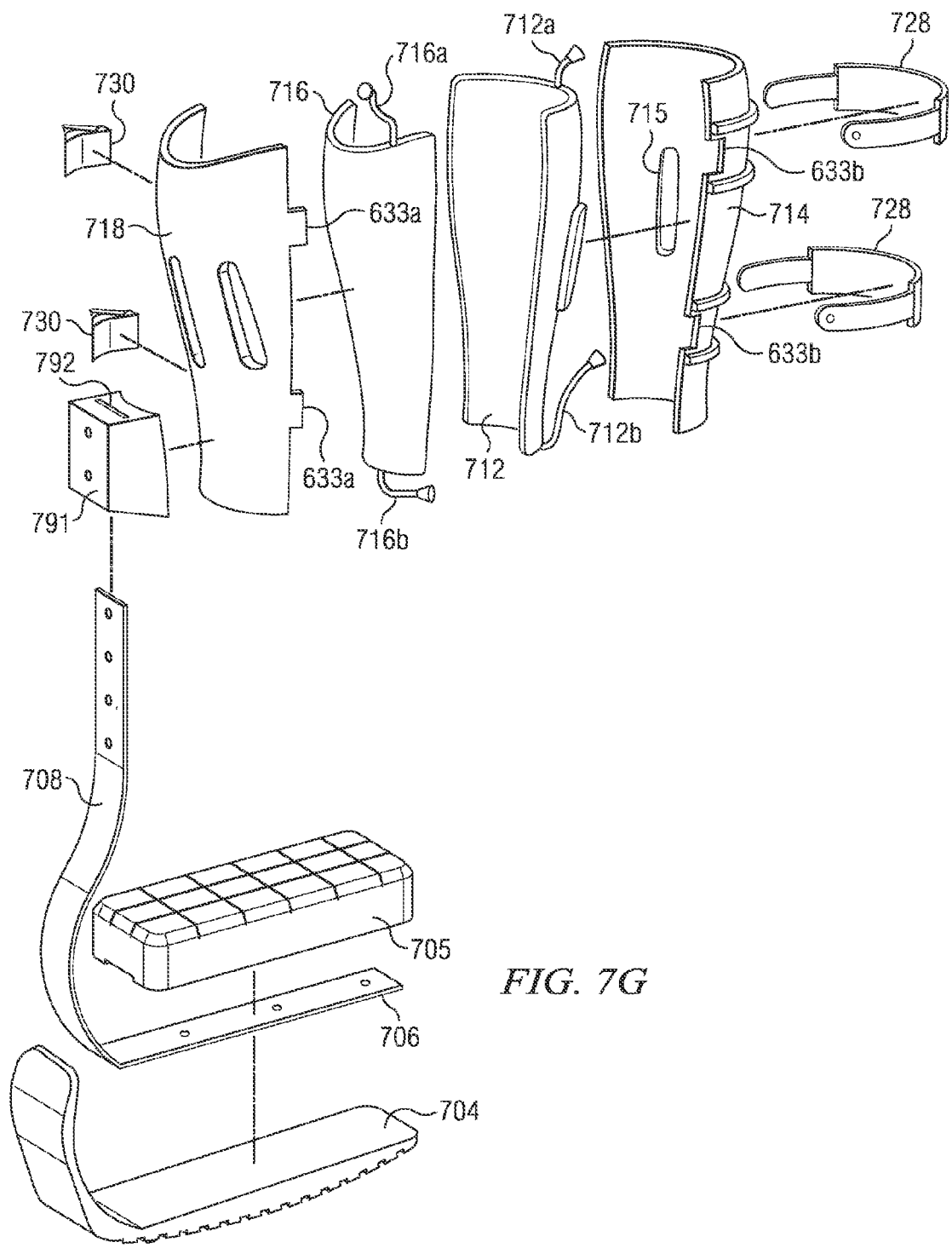
FIG. 7G illustrates an exploded view of the device for ambulation of a subject shown in FIG. 7A according to a specific example embodiment of the disclosure.

FIGS. 7F and 7G illustrate exploded views of an example load redistribution system 702 for ambulation of a subject having a lower extremity impairment, in accordance with embodiments of the present disclosure. As shown in FIG. 7G, pad shell 718 may include protrusions 733a that complement slots 733b in pad shell 714. When pad shells 714 and 718 come together (e.g., around a subject's leg), protrusions 733a fit into corresponding slots 733b and may stabilize the pad shell sections relative to each other.

Figure 7H:
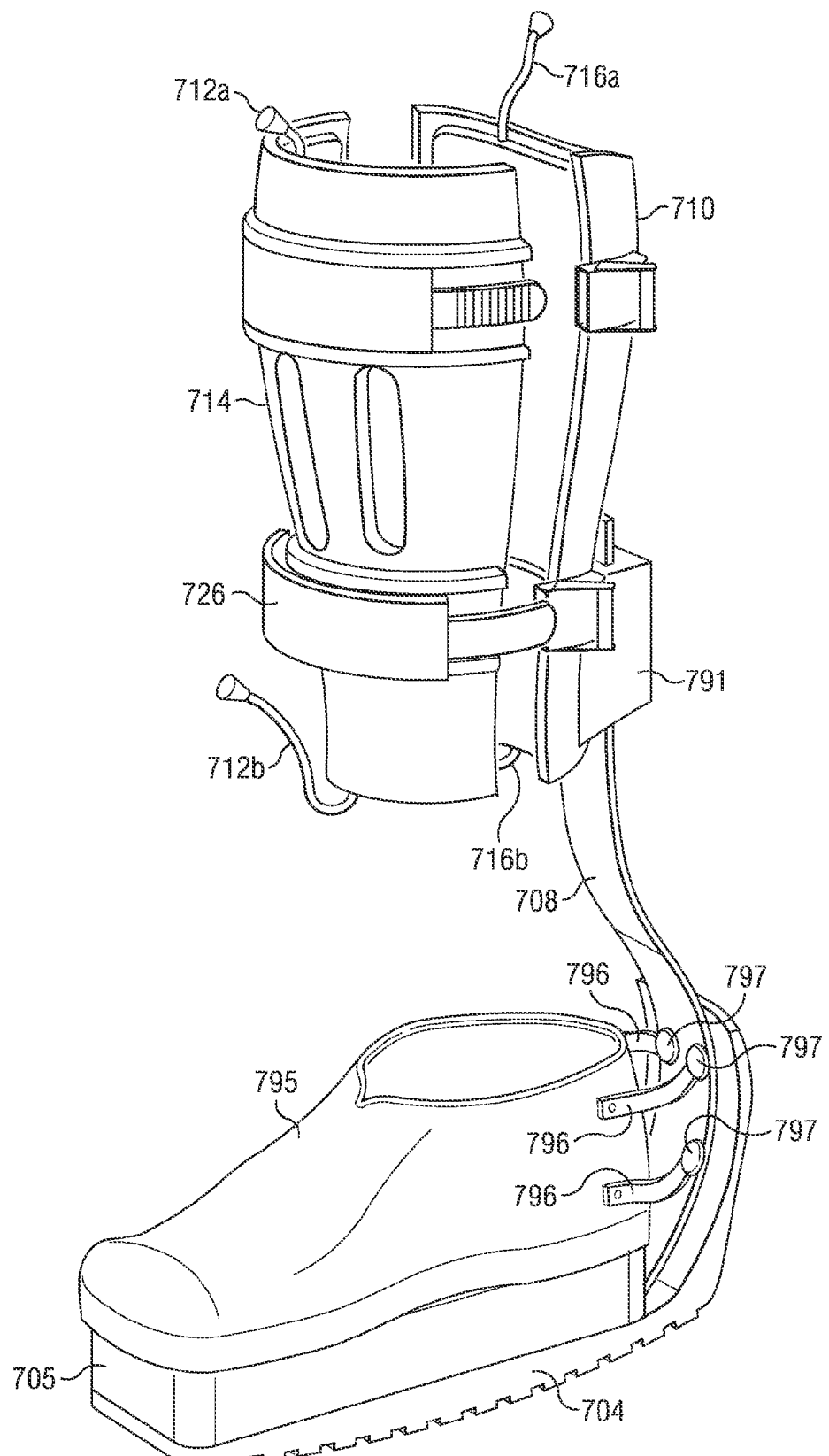
FIG. 7H illustrates a generally isometric view of the device for ambulation of a subject shown in FIG. 7A according to a specific example embodiment of the disclosure.

FIG. 7H illustrates an example load redistribution system 702 for ambulation of a subject having a lower extremity impairment, in accordance with embodiments of the present disclosure. As shown in FIG. 7H, system 702 may include shell 795 configured to shield and/or protect a subject's foot from incidental contact with other objects. Shell 795 may be secured to strut 708 with straps 796 and snaps 797 as illustrated. Additional straps, snaps, and/or other fasteners may be added to secure shell 795 (e.g., between shell 795 and outsole 704 and/or platform 708.

Figure 8A:
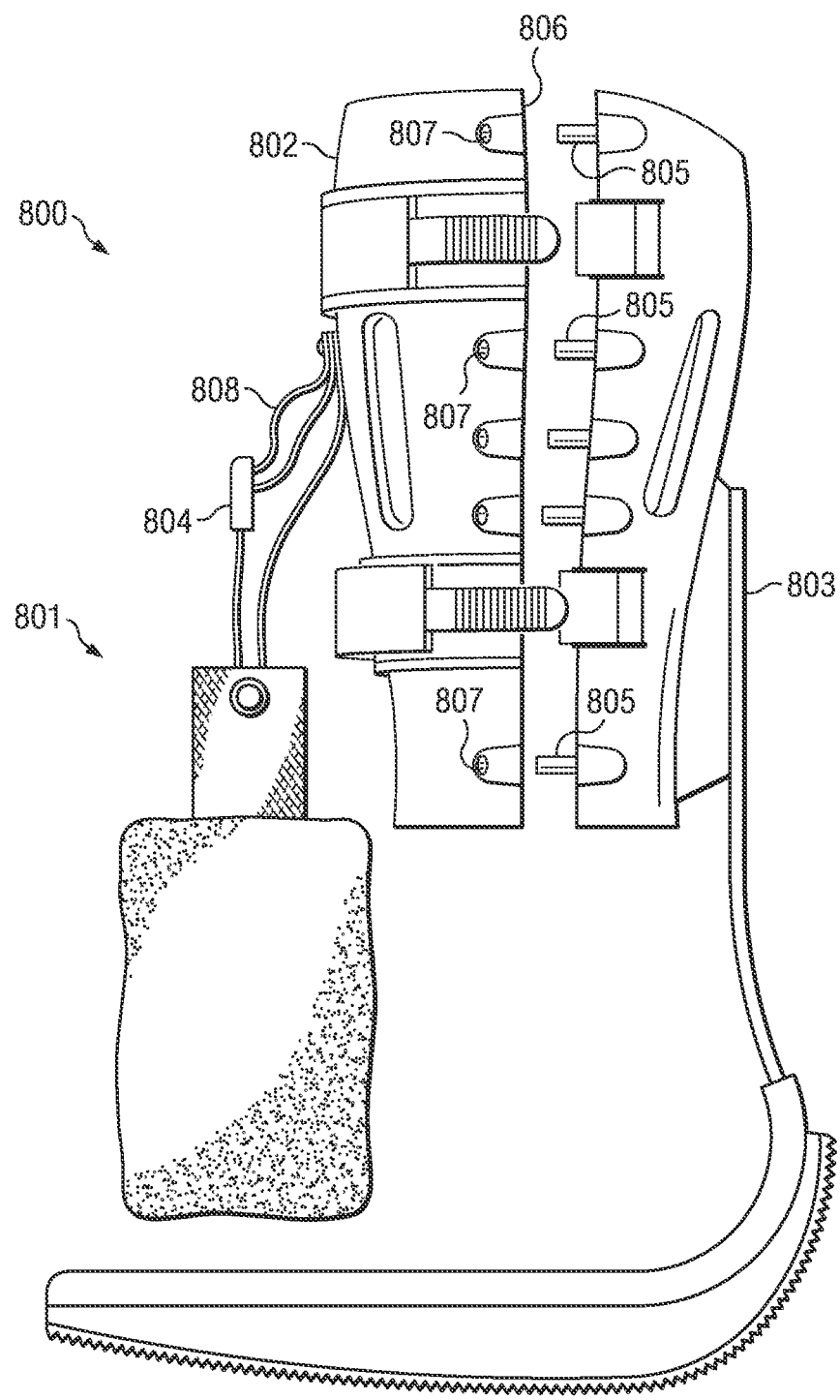
FIG. 8A illustrates a generally side view of a device for ambulation of a subject having an impaired lower extremity according to a specific example embodiment of the disclosure.

FIG. 8A illustrates an example load redistribution system 800 for ambulation of a subject having a lower extremity impairment, in accordance with embodiments of the present disclosure. As shown in FIG. 8A, system 800 may include a sling 801 configured to secure a subject's foot in a particular position (e.g., a non-weight bearing position) for any desirable reason (e.g., patient comfort, protection of an injured or diseased portion of the foot). The sling 801 may attach to at least one cuff 802 and/or at least one strut 803 and its height may be adjusted using a buckle 804. Alignment or guide pins 805 may be included to guide cuff components into proper alignment with each other and to provide further support for the device when it is surrounding the circumference of at least a portion of the subject's leg. For example, a system comprising two cuffs configured to contact each other along at least one edge 806, may include one or more guide pins 805 (e.g., positioned generally perpendicular to the at least one edge) on one cuff and corresponding guide apertures 807 (e.g., sleeves) on the other cuff In some embodiments, a guide pin 805 may slide releasably in a corresponding guide aperture 807. A system may include any desired or required number of guide pins and corresponding guide apertures (e.g., from about 1 pair to about 20 pairs). According to some embodiments, all guide pins may be arranged on one cuff and all guide apertures may be located on a facing cuff In some embodiments, a mixture of guide pins and apertures may be arranged on one cuff with the corresponding guide pins and apertures arranged on the other cuff.

Figure 8B:
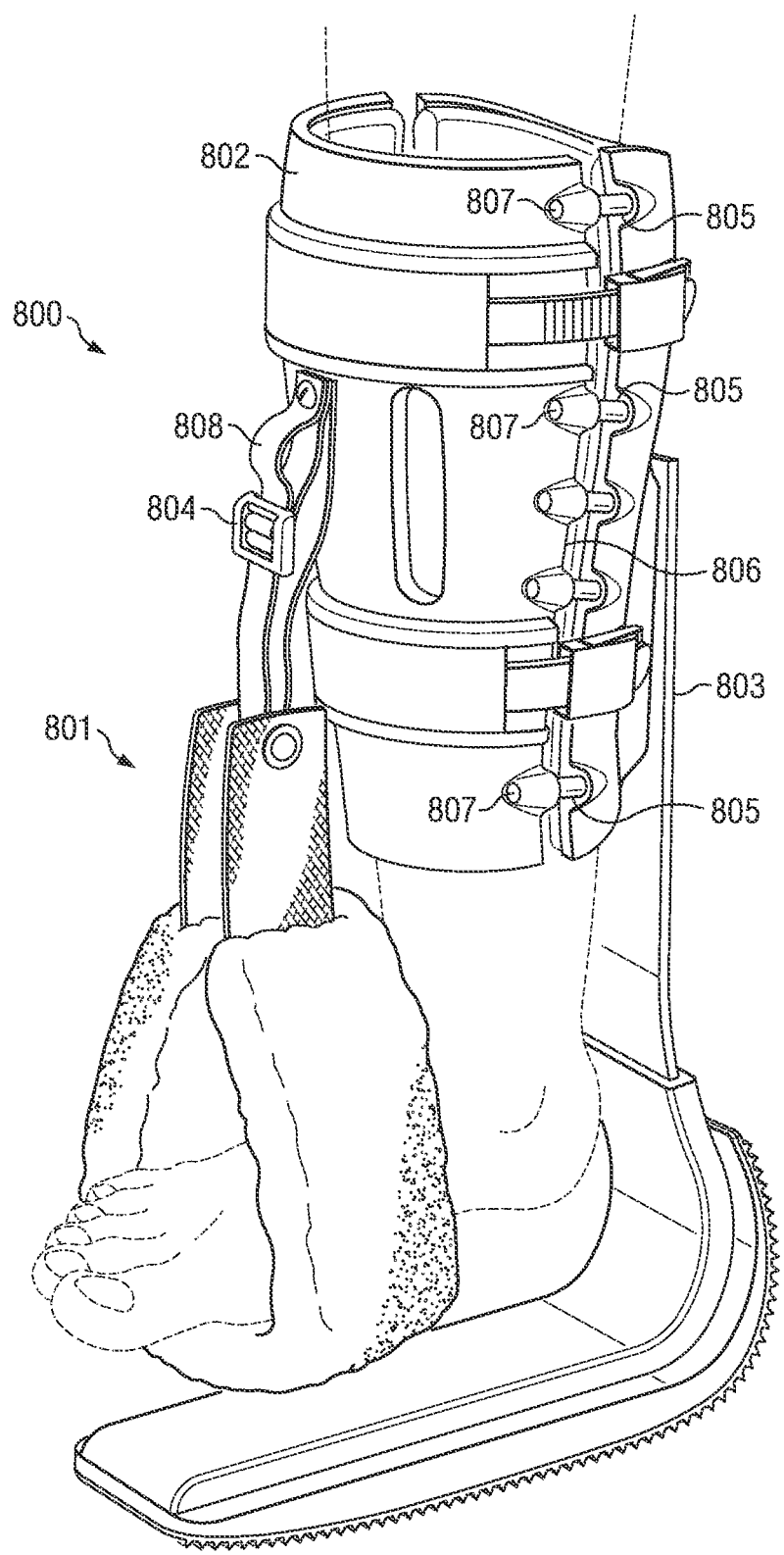
FIG. 8B illustrates a generally isometric view of the device for ambulation of a subject shown in FIG. 8A according to a specific example embodiment of the disclosure.

FIG. 8B illustrates the example load redistribution system 800 of FIG. 8A from a different perspective and also illustrates an example of the foot in the sling 801. As discussed previously, the sling 801 may be used to support and/or immobilize a subject's foot in a desired position without permitting the foot to bear weight. For example, the sling may be used to immobilize the foot in a position that prevents and/or minimizes an Achilles tendon contracture. The sling 801 may attach (e.g., by a slide, spring or adjustable canvas component (e.g., a strap) to avoid permitting the foot to bear weight) to at least one cuff 802 and/or at least one strut 803. In the instance where canvas strap 808 or other similar material is used for attachment, the length of strap 808 may be adjusted using a buckle 804 or any other means known in the art including snaps, clasps and the like. This permits one to adjust the height of the sling and position the foot in the desired configuration with the desired tension. The portion of the sling 801 in contact with the foot may be of any useful material including, but not limited to, synthetic fabrics, plastics, foams, and natural products like cotton or wool. For example, polyurethane, polyethylene, neoprene, ethylene vinyl acetate, silicone, rubber, and combinations thereof may be used. Alignment or guide pins 805 may be included to guide cuff components into proper alignment with each other and to provide further support for the device when it is surrounding the circumference of at least a portion of the subject's leg. For example, a system comprising two cuffs configured to contact each other along at least one edge 806, may include one or more guide pins 805 (e.g., positioned generally perpendicular to the at least one edge) on one cuff and corresponding guide apertures 807 (e.g., sleeves) on the other cuff In some embodiments, a guide pin 805 may slide releasably in a corresponding guide aperture 807. A system, in some embodiments, may include a guide pin/guide aperture system, a sling system, or both a guide pin/guide aperture system and a sling system.

A lower extremity brace may comprise, according to some embodiments, a prosthetic appliance. For example, a lower extremity brace configured to be worn by an amputee, may comprise a portion of the missing appendage. In some embodiments, a lower extremity brace may comprise a strut (e.g., an S-curve strut) having a proximal and a distal end, a cuff attached to the proximal portion of the strut, and a prosthetic appliance (e.g., an artificial foot) attached to the distal end of the strut. In some embodiments, a cuff may be slidably attached to a strut to permit adnustment (e.g., adjustment based on the height of the wearer and/or the length of the residual extremity). An amputee may wear a lower extremity brace in such a way that weight is distributed away from the missing portion of the extremity to a portion of the extremity that remains intact or substantially intact.

As will be understood by those skilled in the art who have the benefit of the instant disclosure, other equivalent or alternative compositions, devices, methods, and systems for redistributing a load can be envisioned without departing from the description contained herein. Accordingly, the manner of carrying out the disclosure as shown and described is to be construed as illustrative only.

Persons skilled in the art may make various changes in the shape, size, number, and/or arrangement of parts without departing from the scope of the instant disclosure. For example, the position and number of struts, pads, collars, and/or cuffs may be varied. In some embodiments, pads, pad shells, collars, and/or cuffs may be interchangeable. Interchangeability may allow the pressure exerted on a lateral surface of a subject's leg to be custom adjusted (e.g., by substituting larger or smaller pads). In addition, the size of a device and/or system may be scaled up (e.g., to be used for adult subjects) or down (e.g., to be used for juvenile subjects) to suit the needs and/or desires of a practitioner. Also, where ranges have been provided, the disclosed endpoints may be treated as exact and/or approximations as desired or demanded by the particular embodiment. In addition, it may be desirable in some embodiments to mix and match range endpoints. All or a portion of a device and/or system for redistributing a load may be configured and arranged to be disposable, serviceable, interchangeable, and/or replaceable. These equivalents and alternatives along with obvious changes and modifications are intended to be included within the scope of the present disclosure. Accordingly, the foregoing disclosure is intended to be illustrative, but not limiting, of the scope of the disclosure as illustrated by the following claims.

What is claimed is:

1. A method for facilitating ambulation of a subject having a leg with an impaired lower extremity, the method comprising:
    suspending at least a portion of the impaired lower extremity in a non-weight bearing position using a load redistribution system; and
    redistributing the weight to one or more unimpaired regions of the leg using the load redistribution system, the load redistribution system comprising:
    a platform;
    at least one vertical support fixed to the platform and extending upwardly from the platform; and
    at least one cuff mounted to the at least one strut at a position sufficient to suspend the at least a portion of the impaired lower extremity in a non-weight-bearing position above the platform during ambulation, wherein the platform, the at least one strut, and the at least one cuff are configured to (a) bear at least the subject's full weight and (b) distribute the weight born to at least a portion of the subject's leg other than the subject's foot, and wherein components of the at least one cuff are releasably connected in proper alignment using alignment pins,
    wherein the impaired lower extremity comprises an amputation residual limb.

2. A method for facilitating ambulation of a subject according to claim 1, wherein the at least one vertical support comprises a strut positioned relative to the subject's leg on which the system is worn opposite the subject's sagittal plane or opposite the subject's coronal plane.

3. A method for facilitating ambulation of a subject according to claim 1, wherein the at least one vertical support comprises a strut positioned generally behind the subject's leg on which the system is worn.

4. A method for facilitating ambulation of a subject according to claim 1, wherein the strut has an S-curve profile.

5. A method for facilitating ambulation of a subject according to claim 1, wherein the at least one vertical support comprises a strut positioned generally outside the subject's leg on which the system is worn.

6. A method for facilitating ambulation of a subject according to claim 1, wherein the at least one vertical support extends distal to the subject's foot.

7. A method for facilitating ambulation of a subject according to claim 1, wherein the at least one cuff comprises an anterior shell, an opposing posterior shell, and at least one tension adjustment fastener configured to releasably connect the anterior shell and the posterior shell, wherein the anterior shell and the posterior shell are configured to combine to surround the circumference of the subject's leg.

8. A method for facilitating ambulation of a subject according to claim 7, wherein the anterior shell comprises at least one fastener guide positioned across the anterior surface of the anterior shell and configured to receive at least a portion of the at least one tension adjustment fastener.

9. A method for facilitating ambulation of a subject according to claim 7, wherein the anterior shell and/or the posterior shell comprise a moldable plastic selected from the group consisting of a thermoplastic, a thermosetting plastic, and combinations thereof.

10. A method for facilitating ambulation of a subject according to claim 7, wherein the anterior shell or the posterior shell is adjustably mounted to the at least one vertical support.

11. A method for facilitating ambulation of a subject according to claim 7, wherein the at least one cuff further comprises at least one pad fixed to the anterior shell and at least one pad fixed to the posterior shell.

12. A method for facilitating ambulation of a subject according to claim 11, wherein the pads independently comprise a material selected from the group consisting of polyurethane, polyethylene, neoprene, ethylene vinyl acetate, foam, silicone, rubber, and combinations thereof.

13. A method for facilitating ambulation of a subject according to claim 7, wherein the at least one cuff further comprises at least one bladder fixed to the anterior shell and at least one bladder fixed to the posterior shell.

14. A method for facilitating ambulation of a subject according to claim 13, wherein at least one of the bladders is at least partially filled with a fill material.

15. A method for facilitating ambulation of a subject according to claim 14, wherein the fill material comprises a foam.

16. A method for facilitating ambulation of a subject according to claim 1, wherein redistributing the weight to one or more unimpaired regions of the leg comprises redistributing the weight to one or more lateral surfaces of the leg.

17. A method for facilitating ambulation of a subject according to claim 16, wherein redistributing the weight to one or more lateral surfaces of the leg further comprises adjusting the pressure applied to at least one lateral surface.

18. A method for facilitating ambulation of a subject having a leg with an impaired lower extremity, the method comprising:
    contacting the leg with a load redistribution system to suspend at least the impaired lower extremity in a non-weight bearing position; and
    redistributing at least the weight of the subject during ambulation to one or more unimpaired regions of the leg, the load redistribution system comprising:
    a platform;
    at least one vertical support fixed to the platform and extending upwardly from the platform; and
    at least one cuff adjustably mounted to the at least one strut at a position sufficient to suspend the at least a portion of the impaired lower extremity in a non-weight-bearing position above the platform during ambulation, wherein the platform, the at least one strut, and the at least one cuff are configured to (a) bear at least the subject's full weight and (b) distribute the weight born to at least a portion of the subject's leg other than the subject's foot wherein the at least one cuff comprises at least one collar having opposite ends spaced apart and a tension adjustment fastener corresponding to each collar, each tension adjustment fastener configured to releasably connect the opposing ends of the corresponding collar, wherein each collar and corresponding tension adjustment fastener are together configured to surround the circumference of the subject's leg, wherein the impaired lower extremity comprises an amputation residual limb.

19. A method for facilitating ambulation of a subject according to claim 18, wherein the at least one vertical support comprises a single vertical support.

20. A method for facilitating ambulation of a subject according to claim 19, wherein the single vertical support is sized to extend distal to the subject's foot.

* * * * *